United States Patent [19]

Becker et al.

[11] Patent Number: 5,689,039
[45] Date of Patent: Nov. 18, 1997

[54] PLANT PEPTIDE TRANSPORT GENE

[75] Inventors: Jeffrey M. Becker; Gary Stacey, both of Knoxville, Tenn.

[73] Assignee: The University of Tennessee Research Corporation, Knoxville, Tenn.

[21] Appl. No.: 212,188

[22] Filed: Mar. 16, 1994

[51] Int. Cl.[6] .......................... A01H 4/00; C07K 14/415; C12N 5/14; C12N 15/29
[52] U.S. Cl. .................................. 800/205; 800/DIG. 15; 536/23.6; 435/320.1; 435/240.4; 435/172.3; 435/172.1; 530/370
[58] Field of Search ........................ 435/320.1, 172.3, 435/240.4, 172.1; 536/23.2, 23.6; 800/205, DIG. 15; 530/370

[56] References Cited

PUBLICATIONS

Peptide transport and chemotaxis in *Escherichia coli* and *Salmonella typhimurium*: characterization of the dipeptide permease (Dpp) and the dipeptide-binding protein, Abouhamad, W.N., et al., *Mol. Microbiol.* 5:1035–1047 (1991).
The ami locus of the Gram-positive bacterium *Streptococcus pneumoniae* is similar to binding protein-dependent transport operons of Gram-negative bacteria, Alloing, G. et al., *Mol. Microbiol.* 4:633–644 (1990).
Genetic Analysis of *Escherichia coli* Oligopeptide Transport Mutants, Andrews, J.C. et al., *J. Bacteriol.* 161:484–492 (1985).
Transport and Utilization of Peptides by Yeast, Becker, J.M. et al., In: *Microorganisms and Nitrogen Sources*, Payne, J.W. (ed.), John Wiley and Sons, Inc., pp. 257–279 (1980).
Genetic Characterization and Molecular Cloning of the Tripeptide PermeASE (TPP) Genes of *Salmonella typhimurium*, Gibson, M.M. et al., *J. Bacteriol.* 160:122–130 (1984).
12 Plant Peptides, Higgins, C.F. et al., In: *Encyclopedia of Plant Physiology, N.S.*, vol. 14A, Boulter, D. et al. (eds.) Springer, NY, pp. 438–458 (1982).
Transport and Utilization of Amino Acids and Peptides by Higher Plants, Higgins, C.F. et al., In: *Microorganisms and Nitrogen Sources*, Payne, J.W. (ed.), John Wiley and Sons, Inc., pp. 211–256 (1980).
Peptide uptake by *Salmonella typhimurium*: The periplasmic oligopeptide-binding protein, Hiles, I.D. et al., *Eur. J. Biochem.* 158:561–567 (1986).
Molecular Characterization of the Oligopeptide Permease of *Salmonella typhimurium*, Hiles, I.D. et al., *J. Molec. Biol.* 195:125–142 (1987).
Isolation and characterization of S. cerevisiae mutants deficient in amino acid-inducible peptide transport, Island, M.D. et al., *J. Bacteriol.* 169:2132–2136 (1987).
Regulation of Dipeptide Transport in *Saccharomyces cerevisiae* by Micromolar Amino Acid Concentrations, Island, M.D. et al., *Curr. Genet.* 20:457–463 (1991).
Identification of the Polyamine-induced Protein as a Periplasmic Oligopeptide Binding Protein, Kashiwagi, K. et al., *J. Biol. Chem.* 265:8387–8391 (1990).
Isolation of a Peptide Transport-Deficient Mutant of Yeast, Marder, R. et al., *J. Bactiol.* 131:906–916 (1977).

A *Bacillus subtilis* dipeptide transport system expressed early during sporulation, Mathiopoulos, C. et al., *Mol. Microbiol.* 5:1903–1913 (1991).
Transmembrane Transport of Small Peptides, Matthews, D.M. et al., *Curr. Top. Membr. Transp.* 14:331–425 (1980).
Mechanism of Action of Nikkomycin and the Peptide Transport System of *Candida albicans*, McCarthy, P.J. et al., *J. Gen. Micro.* 131:775–780 (1985).
Relative Rates of Transport of Peptidyl Drugs by *Candida albicans*, McCarthy, P.J. et al., *Antimicrob. Agents Chemother.* 28:494–499 (1985).
Anti-Candida Activity of Polyoxin: Example of Peptide Transport in Yeasts, Mehta, R.J. et al., *Antimicrob. Agents Chemother.* 25:373–374 (1984).
Transport and Hydrolysis of Peptides in *Saccharomyces cerevisiae*, Moneton, P. et al., *J. Gen. Micro.* 132:2147–2153 (1986).
Utilization of Methionine-containing Peptides and Their Derivatives by a Methionine-requiring Auxotroph of *Saccharomyces cerevisiae*, Naider, F. et al., *J. Biol. Chem.* 249:9–20 (1974).
Peptide Transport in *Candida albicans*: Implications for the Development of Antifungal Agents, Naider, F. et al., In: *Current Topics in Medial Mycology*, vol. II, McGinnis, M.M. (ed.) (1987).
Oligopeptide Transport in *Escherichia coli*, Payne, J.W. et al., *J. Biol. Chem.* 243:3395–3403 (1968).
Size Restriction on Peptide Utlization in *Escherichia coli*, Payne, J.W. et al., *J. Biol. Chem.* 243:6291–6299 (1968).
Isolation and identification of proteins from the peptide-transport carrier in the scutellum of germinating barley (*Hordeum vulgare* L.) embryos, Payne, J.W. et al., *Planta* 170:263–271 (1987).
Studies on drug targeting in the pathogenic fungas *Candida albicans*: peptide transport mutants resistant to polyoxins, nikkomycins and bacilysin, Payne, J.W. et al., *FEMS Microbiol. Letts.* 28:55–60 (1985).
The oligopeptide transport system of *Bacillus subtilis* plays a role in the initiation of sporulation, Perego, M. et al., *Mol. Microbiol.* 5:173–185 (1991).
Isolation and Characterization of a *Saccharomyces cerevisiae* Peptide Transport Gene, Perry, Jack R., et al., *Molecular and Cellular Biology*, vol. 14 (1994).
Structure and function of the yeast URA3 gene: expression in *Escherichia coli*, Rose, M.D. et al., *Gene* 29:113–124 (1984).
The spoOk Locus of *Bacillus subtilis* Is Homologous to the Oligopeptide Permease Locus and Is Required for Sporulation and Competence, Rudner, D.Z. et al., *J. Bacteriol.* 173:1388–1398 (1991).

(List continued on next page.)

*Primary Examiner*—Che S. Chereskin
*Attorney, Agent, or Firm*—Weiser and Associates P.C.

[57] ABSTRACT

A plant peptide transport gene and its nucleotide sequence are disclosed. The gene may be used to confer herbicide resistance to plants, and to render plants resistant to insect pests. The invention also relates to plants that possess non-naturally occurring alleles of peptide transport gene.

24 Claims, 7 Drawing Sheets

PUBLICATIONS

The Herbicide Sensitivity Gene CHL1 of Arabidopsis Encodes a Nitrate–Inducible Nitrate Transporter, Tsay, Y–F. et al., *Cell* 72:705–713 (1993).

Sensitivity to Nikkomycin Z in *Candida albicans*: Role of Peptide Permeases, Yadan, J.C. et al., *J. Bacteriol.* 160:884–888 (1984).

Abouhamad, et al (1991) Molecular Miciobiology 5(5):1035–1047.

Perry, et al (Jan. 1994) Molecular and Cellular Biology 14(1):104–115.

A Dictionary of Genetic Engineering, S. G. Oliver and J.M. Ward, Cambridge University Press, Cambridge, 1985, p. 20.

```
GCGGCCGCCAGTGTGAGTAATTTAGGAGAAATTCAAAAACCTTGAGTGGAAACTCCTCATCGTTCGTATAATAATCGTTGACCTCTTTTGTTGGAGTTG     -551
GGACTTTCTCCACACTTCACATACACACTTTAATTTCCAAGTATTATTTATTAAGGAAAAATTTTCATTCTAAAAATTTTCTTTTTAT               -448
TATTATTGTCATAAATACTATTGTTGTTGTATATTTTTGTAATACCCTTCTCACTCACTTCATATTTCTTACTCTTAGTTGAG                    -345
TTAGTCGGCCTTCGATACACATATAAAAGTGTTATTTAAACTTGTTTTGTGAATTCACTGTGTAATTAGTTGACTAATAATTATTATTA              -242
TTTTTGATCTATTCTTTTCGTTTCGTACTACATTTTTTTAAATCTTTCGCTTGTTATTTCTTCTCCTTTTTATTATTTAATATTCG                 -139
CCTCTTTGTTTCGTTCATTGTAATATTTAATCCAAAAATTGTTCTTGAAACTCTGTCATTCTTCTCTTTTTATTATTTTGATTTCATACG              -36
ATCGATTCCTACACATTCAATTACCGTGTGTTACA ATG AGT AGT ATT GAA GAA CAA ATT ACG AAA TCG GAC TCC GAT TTC ATC ATT    51
                                     M   S   S   I   E   E   Q   I   T   K   S   D   S   D   F   I   I

TCA GAA GAT CAA TCC TAC TTA AGC AAG GAG AAA AAG GCT GAT GGT TCT GCC ACC ATC AAC CAA GCT GAC GAA CAA TCC   129
 S   E   D   Q   S   Y   L   S   K   E   K   K   A   D   G   S   A   T   I   N   Q   A   D   E   Q   S

TCC ACC GAT GAA CTC CAA AAA TCC ATG TCC AAT GGC GTC CTC GTC AAT GGT GAC TTA TAC CCT TCT CCT ACC GAA GAA   207
 S   T   D   E   L   Q   K   S   M   S   N   G   V   L   V   N   G   D   L   Y   P   S   P   T   E   E

GAA TTA GCC ACC CTT CCT AGT GTT TGC GGT ACT ATT CCT TGG AAA GCC TTT ATT ATC ATT GTC GAG CTT TGC GAA   285
 E   L   A   T   L   P   S   V   C   G   T   I   P   W   K   A   F   I   I   I   V   E   L   C   E

CGT TTC GCT TAC TAT GGA CTC ACT GTT CCC TTT CAA AAT TAT ATG CAA TTC TTC ACA TTT TTT TGG TGT TAT GTC CCG GTT GGC GCT   363
 R   F   A   Y   Y   G   L   T   V   P   F   Q   N   Y   M   Q   F   F   T   F   F   W   C   Y   V   P   V   G   A

CTT AAT TTA GGC GAA ACC GGT GCT GAC GGT CTT TCT AAT TTC TTT AAT ACC ATT GTT TGC TCT GCT ATT TAC TTT ATT GGT ATC TTG   441
 L   N   L   G   E   T   G   A   D   G   L   S   N   F   F   N   T   I   V   C   S   A   I   Y   F   I   G   I   L

GCA CTT ATT GCT GAT CAA TTC CTT GGT AGG TAC AAT GTT GTC ATT TAC TTT ATT GGT ATC TTG   519
 A   L   I   A   D   Q   F   L   G   R   Y   N   V   V   I   Y   F   I   G   I   L
```

FIG. 1

| FIG. 1A |
|---------|
| FIG. 1B |
| FIG. 1C |

```
ATT CTT ACA TGT ACT GCT ATT CCT TCT GTC ATT GAT GCC GGA AAA AGT ATG GGT GGG TTT GTC GTC TCT TTG ATC ATC  597
 I   L   T   C   T   A   I   P   S   V   I   D   A   G   K   S   M   G   G   F   V   V   S   L   I   I

ATT GGG CTT GGA ACC GGT ATC AAA TCC AAT GTT TCC CCC TTG ATG GCT GAA CAG CTT CCA AAA ATT CTT CCT TAT  675
 I   G   L   G   T   G   I   K   S   N   V   S   P   L   M   A   E   Q   L   P   K   I   L   P   Y

GTA AAG ACA AAA AAT GGT AGC AAG GTC ATT GTT GAC CCA GTC ACC TCT CGT GCC TAT ATG ATT TTC TAC  753
 V   K   T   K   N   G   S   K   V   I   V   D   P   V   T   S   R   A   Y   M   I   F   Y

TGG ACA ATT AAC GTC GGT TCT CTC TCC GTA TTA GCC ACA ACT AGT TTG GAA AGT ACT AAA GGT TTT GTT TAC CGA TAC  831
 W   T   I   N   V   G   S   L   S   V   L   A   T   T   S   L   E   S   T   K   G   F   V   Y   R   Y

TTG CTT CCC TTG TGC GTC TTT ATC CCC TTA ATT ATT TTG GCT GTT AGT AAG ACA GCT TTT ACA AGC ACA CTC CTC  909
 L   L   P   L   C   V   F   I   P   L   I   I   L   A   V   S   K   T   A   F   T   S   T   L   L

CCT CCG GTT CCA TCT TTG CTA CTG TTG GTC AAG TGT TCT TCC CTG CTC AAA ACA AAT TTA ATC TCG AAA AAA CTA  987
 P   P   V   P   S   L   L   L   L   V   K   C   S   S   L   L   K   T   N   L   I   S   K   K   L

AAC CAT CTT GCA CTA CTA CTT AAA ACT TTT CTC TTG GAG CGT TAC GTC AAG TAC CCT ACT TAT TGG GAT CAG GAT GAC TTG TTT ATC GAC GAA TTG 1065
 N   H   L   A   L   L   L   K   T   F   L   L   E   R   Y   V   K   Y   P   T   Y   W   D   Q   D   D   L   F   I   D   E   L

GCC TTA CGC GCC TGC AAA ACT TTT CTC TTT CAA ACG GGT AAT GTC TCT AAC GAT CTT TTC CAA GCC TTC GAT TCA ATC GCC TTG ATT ATT 1143
 A   L   R   A   C   K   T   F   L   F   Q   T   G   N   V   S   N   D   L   F   Q   A   F   D   S   I   A   L   I   I

TCT CAA GCT GGA CAA ATG CAA ACG GGT AAT GTC TCT AAC GAT CTT TTC CAA GCC TTC GAT TCA ATC GCC TTG ATT ATT 1221
 S   Q   A   G   Q   M   Q   T   G   N   V   S   N   D   L   F   Q   A   F   D   S   I   A   L   I   I
```

FIG. 1C

```
 -33  gcggccgccagtgtgagtaatttagcgaaaacgatgggttccatcgaagaagaagcaaga   27
                                      M  G  S  I  E  E  E  A  R 28  cctctcatcgaagaaggtttaattttacaggaagtgaaattgtatgctgaagatggttca   87
      P  L  I  E  E  G  L  I  L  Q  E  V  K  L  Y  A  E  D  G  S 88  gtggacttttaatggaaaaccaccattgaaggagaaactggaaaagtttggaattgtcct  147
      V  D  F  N  G  N  P  P  L  K  E  K  L  E  K  F  G  N  W  K  A  C  P 148  tttattcttggtaatgaatgttgagaggctagctactatggtactgttgctgggaattaa  207
      F  I  L  G  N  E  C  C  E  R  L  A  Y  Y  G  T  V  A  G  N  L 208  atcacttaccttcaccactaagctttcacagaaatgtttctgctgctacaaacgttacc  267
      I  T  Y  L  T  T  K  L  H  Q  N  V  S  A  A  T  N  V  T 268  acatggcaagggacttactgaccatcgcttgttatctcattggagctgttcatttcatcg  327
      T  W  Q  G  T  Y  L  P  L  Y  F  S  L  I  G  A  V  L  A  D  A  Y 328  tgggactggaagcgttactccgaacagctcggatgtgttcttggttgccgatcgtctgcg  387
      W  G  R  Y  W  T  I  A  C  F  S  G  I  Y  F  G  M  S  A 388  ttaactctttcagctcagtccggcattgaagcttgatcctcatcttaccttggtgacttgt  447
      L  T  L  S  A  S  V  P  A  L  K  P  A  E  C  I  D  F  C 448  ccatctgcaagctcagcgcagtatgcgattgtcttttggtgggctttcttaccttcttt  507
      P  S  A  T  P  A  Q  Y  A  M  F  F  G  G  L  Y  L  A  L 508  ggaactggaggtatcaaacgtgtgtctcatcagttcggtgccgatcagtttgatgacacg  567
      G  T  G  G  I  K  P  C  V  S  S  F  G  A  D  Q  F  D  D  T 568  gacttctcggaacgagttagaaaagcttcgttctgtttaactggtttacttctcctcaat  627
      D  S  R  E  R  V  R  K  A  S  F  N  W  F  Y  F  S  I  N
```

FIG. 2

| FIG. 2A |
|---------|
| FIG. 2B |
| FIG. 2C |

FIG. 2A

```
628  attggagcacttgtgttcatctagtttggattcaagagaatcggggtggggt  687
      I  G  A  L  V  S  S  L  V  W  I  Q  E  N  R  G  W  G
688  ttagggtttggatacaacagtgttcatgggactagccagtgccaagtttcttttggc  747
      L  G  F  F  G  I  P  T  V  F  M  G  L  A  I  A  S  F  F
478  acacctctttatagttcagaaactggaggagcccctataactggatttccaagtc  807
      T  P  L  Y  R  F  Q  K  P  G  G  P  I  T  R  I  S  Q  V
808  gtggttgcttcgttccggaaatcgtctgtcaaagtcgtcctgaagacgtccacacttctgtat  867
      V  A  S  F  R  K  S  V  K  P  E  D  A  T  L  Y
868  gaaaactcaagacaagaagtcgctggaagtagaaaaatcgagcatacgatgat  927
      E  T  Q  D  K  N  S  A  I  A  G  S  R  K  I  E  H  T  D  D
928  tgccagtatctcgtggagactcgtgctattgtatcgaagaactcaagattctgatccga  987
      C  Q  Y  L  D  K  A  A  V  I  S  E  E  L  K  I  L  I  R
988  tcaactcgtggagactcgtggctattgctaggttcacgg ttacgcaaatcaagatt cgacgattctccaa  1047
      S  N  S  W  R  L  C  T  V  T  Q  V  E  L  Y  A  Q  M  S  T
1048  atgttccaatctgggcttggtatcattcagcttgggtccgcttcattccagcttcctcct  1107
       M  F  P  I  W  A  S  G  I  I  F  S  A  V  Q  L  P  P
1108  atgtttgttcaacaaggcgagccattgaactgcaaagttggatcatcaagcgtacgacgg  1167
       M  F  V  Q  Q  G  R  A  M  N  C  K  I  G  S  F  Q  L  Y  D  R
1168  gcagcactcgggacattgtccttagcaagaagtcacaggagtagacaggattcactggataccaa  1227
       A  A  L  T  F  D  T  A  S  V  I  W  P  L  Y  E  I  Q
1228  ttcatcgttccctgttttgtctgttctgttctgtatggcagtgcagctatcgtcgaa  1287
       F  I  V  P  L  A  R  K  F  T  G  V  D  K  G  F  T  E
1288  agaatgggaattggtctgttttgtctgttctgtatggcagctgcagctatcgtcgaa  1347
       R  M  G  I  G  L  F  V  S  V  L  C  M  A  A  A  I  V  E
```

*FIG. 2B*

```
1348  atcatcgtctccatatggccaacgatcttggattagtcgagtcaggagcccagttccc  1407
       I  I  R  L  H  M  A  N  D  L  G  L  V  E  S  G  A  P  V  P
1408  atatccgtctgtggcagattccacagtacttcattctcgtgcagccgaagtattctac  1467
       I  S  V  W  Q  I  P  Q  Y  F  I  L  G  A  A  E  V  F  Y
1468  ttcatcggtcagctcgagttcttccagaccaatctccagatgcaatgagaagcttgtgc  1527
       F  I  G  Q  L  E  F  F  Q  D  S  P  D  A  M  R  S  L  C
1528  agtgccttagctgtctttttgaccaatgtaactacttgagctcgttgatctctcacg   1587
       S  A  L  A  L  F  T  N  Y  L  S  S  L  I  T
1588  ctcgtgacttattttacaacaagaaatgggcaagaaggttggatttcggataatctcaat 1647
       L  V  T  Y  F  T  T  R  N  G  Q  E  G  W  I  S  D  N  L  N
1648  tcaggtcatctcttctctgattactttctggctcttggtcttagccttgtcgtagtggcg 1707
       S  G  H  L  F  L  D  Y  F  W  L  A  G  L  S  L  V  N  M  A
1708  gtttacttctctgctgtaggtataagcaaaagaaagcttgtttcttcaactgtctgt   1767
       V  Y  F  S  A  A  R  Y  K  Q  K  K  A  S  S  L  *
1768  tatctatcttcattacataaaagtttgttttcttcaatttcaaaagttaactgtctgta  1827
1828  tcaataaacaattgctgtgtactttccttttcaatttcaatttaagtcgcctaaat      1887
1888  tactcacactggcggccgc 1906
```

*FIG. 2C*

PLANT PEPTIDE TRANSPORT GENE

FIELD OF THE INVENTION

The invention relates to plant molecular genetics, and more specifically, to the cloning of a plant peptide transport gene. The plant peptide transport gene may be used to confer herbicide resistance, and pest resistance to recipient plants. The gene may also be used to facilitate the delivery of desired molecules into plants. The invention pertains to the peptide transport gene, to plants that contain the gene, and to methods for using the gene.

BACKGROUND OF THE INVENTION

Peptide uptake is the process by which individual cells are able to transport intact peptides across their plasma membranes. The process is a general physiological phenomenon of bacteria, fungi, plant cells and mammalian cells (Becker, J. M. et al, In: *Microorganisms and Nitrogen Sources*, Payne, J. W. (ed.), John Wiley and Sons, Inc., pp. 257–279 (1980); Matthews, D. M. et al., *Curr. Top. Membr. Transp.* 14:331–425 (1980)). In every case studied so far, peptide transport is a specific biochemical process in which small peptides ($\leq 6$ amino acids) are transported across a membrane by energy-dependent, saturable carriers.

Three genetically distinct systems of peptide uptake have been identified in gram-negative bacteria. An oligopeptide permease (Opp) system has been identified in bacteria such as *E. coli*, and *S. typhimurium* (Andrews, J. C. et al., *J. Bacteriol.* 161:484–492 (1985); Hogarth, B. G. et al., *J. Bacteriol.* 153:1548–1551 (1983)). The Opp system is capable of transporting peptides having up to 5 amino acid residues, regardless of their side chains (Payne, J. W. et al, *J. Biol. Chem.* 243:3395–3403 (1968); Payne, J. W. et al., *J. Biol. Chem.* 243:6291–6299 (1968)). In contrast, tripeptide permease (Tpp) systems, such as that of *S. typhimurium*, exhibit an apparent affinity for peptides having hydrophobic amino acid residues (Gibson, M. M. et al., *J. Bacteriol.* 160:122–130 (1984)). The third system, a dipeptide permease (Dpp) system, has a preference for transporting dipeptides (Abouhamad, W. N., et al., *Mol. Microbiol.* 5:1035–1047 (1991)). Functionally similar systems have been described in fungi and yeast (Naider, F. et al., In: *Current Topics in Medial Mycology*, volume II, McGinnis, M. M. (ed.) (1987)), but have not been well characterized.

The genes that encode the protein components of the oligopeptide transporters of *E. coil* (Kashiwagi, K. et al, *J. Biol. Chem.* 265:8387–8391 (1990)), *Salmonella typhimurium* (Hiles, I. D. et al., *Eur. J. Biochem.* 158:561–567 (1986); Hiles, I. D. et al, *J. Molec. Biol* 195:125–142 (1987)), *Bacillus subtills* (Rudner, D. Z. et al., *J. Bacteriol.* 173:1388–1398 (1991); Perego, M. et al., *Mol. Microbiol.* 5:173–185 (1991)), *Streptococcus pneumoniae* (Alloing, G. et al., *Mol. Microbiol.* 4:633–644 1990)), and *Lactococcus lactis* as well as two dipeptide permeases, one in *E. coil* (Abouhamad, W. N., et al., *Mol. Microbiol.* 5:1035–1047 (1991)), and the other in *Bacillus subtilis* (Mathiopoulos, C. et al., *Mol. Microbial.* 5:1903–1913 (1991)) have been cloned and sequenced.

The ability of bacteria and plant cells to accumulate peptides has been found to be dependent upon peptide transport systems (Becker, J. M. et al., In: *Microorganisms and Nitrogen Sources*, Payne, J. W. (ed.), John Wiley and Sons, Inc., pp. 257–279 (1980); Matthews, D. M. et al., *Curr. Top. Membr. Transp.* 14:331–425 (1980); Higgins, C. F. et al., In: *Microorganisms and Nitrogen Sources*, Payne, J. W. (ed.), John Wiley and Sons, Inc., pp. 211–256 (1980); Naider, F. et al., In: *Current Topics in Medial Mycology*, volume II, McGinnis, M. M. (ed.) (1987)). These systems are distinct from the mechanisms that mediate the uptake of amino acids.

The existence of peptide transport systems in plants was demonstrated by showing that plants could accumulate non-hydrolyzable, non-physiological peptide substrates, intact and against a concentration gradient (Higgins, C. F. et al., *Planta* 134:205–206 (1977); Higgins, C. F. et al., *Planta* 136:71–76 (1977); Higgins, C. F. et al, *Planta* 138:211–216 (1978); Higgins, C. F. et al., *Planta* 142:299–305 (1978); Sopanen, T. et al., *FEBS Lett.* 79:4–7 (1977)). The transport system was found to exhibit saturation kinetics and to be inhibited by a range of metabolic inhibitors (Higgins, C. F. et al., *Planta* 136:71–76 (1977)). The plant peptide transport system can transport both di- and tripeptides (Sopanen, T. et al., *FEBS Lett.* 79:4–7 (1977); Higgins, C. F. et al., *Planta* 142:299–305 (1978)). Plant peptide transport systems are capable of transporting a wide variety of peptides. These systems exhibit broad transport specificity with respect to amino acid side-chains. The presence of D-amino acids, however, reduces the transport rate, thus indicating that the transporters have strong stereospecificity. Two proteins, approximately 66 D and 41 D, have been suggested as components of the plant peptide transport system in barley grains (Payne, J. W. et al., *Planta* 170:263–271 (1987).

The primary function of peptide transport is to supply amino acids for nitrogen nutrition (Payne, J. W. et al., In: *Microorganisms and Nitrogen Sources*, Payne, J. W. (ed.), John Wiley and Sons, Inc., pp. 257–279 (1980); Matthews, D. M. et al., *Curr. Top. Membr. Transp.* 14:331–425 (1980); Becker, J. M. et al., In: *Microorganisms and Nitrogen Sources*, Payne, J. W. (ed.), John Wiley and Sons, Inc., pp. 257–279 (1980); Adibi, S. A. et al., *Metabolism* 36:1001–1011 (1987); Higgins, C. F. et al., *Planta* 138:211–216 (1978); Sopanen, T. et al., *FEBS Lett.* 79:4–7 (1977); Higgins, C. F. et al., *Planta* 138:217–221 (1978)). In bacteria, peptide transport has, however, also been associated with sporulation (Perego, M. et al., *Mol. Microbiol.* 5:173–185 (1991); Mathiopoulos, C. et al., *Mol. Microbiol.* 5:1903–1913 (1991)); chemotaxis (Manson, M. D. et al., *Nature* 321:253–256 (1986), and the recycling of cell wall peptides (Goodell, E. W. et al., *J. Bacteriol* 169:3861–3865 (1987)).

A variety of plant pathogens attack plants by secreting toxic peptides. A capacity to control peptide transport may permit the development of pathogen-resistant plants. The present invention provides polynucleotide molecules, and methods that may be useful for producing such valuable plants.

SUMMARY OF THE INVENTION

The invention concerns a plant peptide transport gene. The gene mediates the uptake of di- and tri-peptides, and confers upon recipient plants the ability to grow on such peptides. Such a capability may be used to facilitate the delivery of desired molecules, such as proteins, etc. into plant cells. By mutating the gene, it is possible to render a plant resistant to toxic peptides, and thus provide the plant with resistance to herbicides and insect toxins. The present invention is directed to polynucleotides that encode the peptide transport gene, to the encoded protein, to antisense molecules that attenuate the expression of the transport gene, and to methods for using all such compositions to improve plant vitality and resistance. The invention also includes plants having non-naturally occurring alleles of the transport gene.

In detail, the invention provides, a substantially purified nucleic acid molecule containing a polynucleotide portion of a plant gene that encodes a peptide transport protein. The polynucleotide portion may encode a functional transport protein, a non-functional transport protein, or a non-functional fragment of either.

The invention additionally concerns a plant cell containing any of such substantially purified nucleic acid molecules, especially, wherein the polynucleotide portion of the plant gene encodes a non-functional transport protein or a non-functional fragment of a peptide transport protein, and wherein the presence of the polynucleotide impairs a capacity of the cell to transport peptides.

The invention also concerns plants and plant products (fruit, leaves, seeds) containing the above-described plant cells.

The invention also provides a method for increasing the resistance of a plant to an herbicidal peptide which comprises:

A. providing a polynucleotide to cells of the plant, the polynucleotide encoding a mutated peptide transport protein or a fragment of a peptide transport protein, wherein the presence of the polynucleotide impairs a capacity of the cells to transport peptides;

B. permitting the polynucleotide to impair the capacity of the plant cells to transport the herbicidal peptide.

The invention also provides a method for selectively inhibiting the growth of an undesired peptide transport proficient plant relative to the growth of a desired peptide transport deficient plant, the method comprising:

A. providing a peptide to the undesired plant, and optionally also to the desired plant, wherein the peptide comprises a toxic moiety capable of inhibiting the growth of a plant when transported into a cell of the plant; and B. permitting the undesired plant to transport the toxic moiety-containing peptide into its cells and further permitting the transported toxic moiety to mediate the inhibition of the growth of the undesired plant.

The invention further concerns a method for delivering an affector of a plant characteristic to a plant, which comprises:

A. providing a polynucleotide to cells of the plant, the polynucleotide encoding a peptide transport protein, wherein the presence of the polynucleotide provides or augments a capacity of the cells to transport peptides;

B. providing a peptide conjugate to the plant, the conjugate containing a moiety that comprises the affector; and C. permitting the peptide transport protein to mediate the delivery of the affector to the plant.

The invention additionally provides a method for identifying an affector of a plant characteristic which comprises:

A. incubating a candidate affector, the affector being conjugated to a peptide, in the presence of a peptide transport deficient *Saccharomyces cerevisiae* strain;

B. incubating the conjugated candidate affector in the presence of a peptide transport proficient *Saccharomyces cerevisiae* strain; and C. determining whether the candidate affector is capable of affecting a characteristic of the peptide transport proficient *Saccharomyces cerevisiae* strain but is incapable of affecting the characteristic in the peptide transport deficient *Saccharomyces cerevisiae* strain.

The invention also provides a method for identifying polynucleotides that encode a plant peptide transport protein which comprises:

A. introducing a candidate polynucleotide into a peptide transport deficient *Saccharomyces cerevisiae* strain;

B. incubating the peptide transport deficient *Saccharomyces cerevisiae* strain in the presence of a peptide; and C. determining whether the introduction of the candidate polynucleotide is sufficient to permit the *Saccharomyces cerevisiae* strain to mediate the transport of the peptide.

DESCRIPTION OF THE FIGURES

FIG. 1 shows the complete nucleotide sequence of the 2.8 kb insert of Arabidopsis cDNA in plasmid pPTF4. The sequence starts with the complete 5' NotI restriction site and stops four nucleotides past the 3' NotI restriction site. The start and stop codons are highlighted in bold. The deduced amino acid sequence of the ATPTR2Ap protein is represented by the single letter amino acid code appearing below the nucleotide sequence. Amino acids predicted to be hydrophobic segments are underlined.

FIG. 2 shows the complete nucleotide sequence of the 2.0 kb insert of Arabidopsis cDNA in plasmid pDTF1. The sequence starts with the complete 5' NotI restriction site and stops four nucleotides past the 3' NotI restriction site. The deduced amino acid sequence of the ATPTR2Bp protein is represented by the single letter amino acid code appearing below the nucleotide sequence.

DESCRIPTION OF THE PREFERRED EMBODIMENTS

Figure 3:
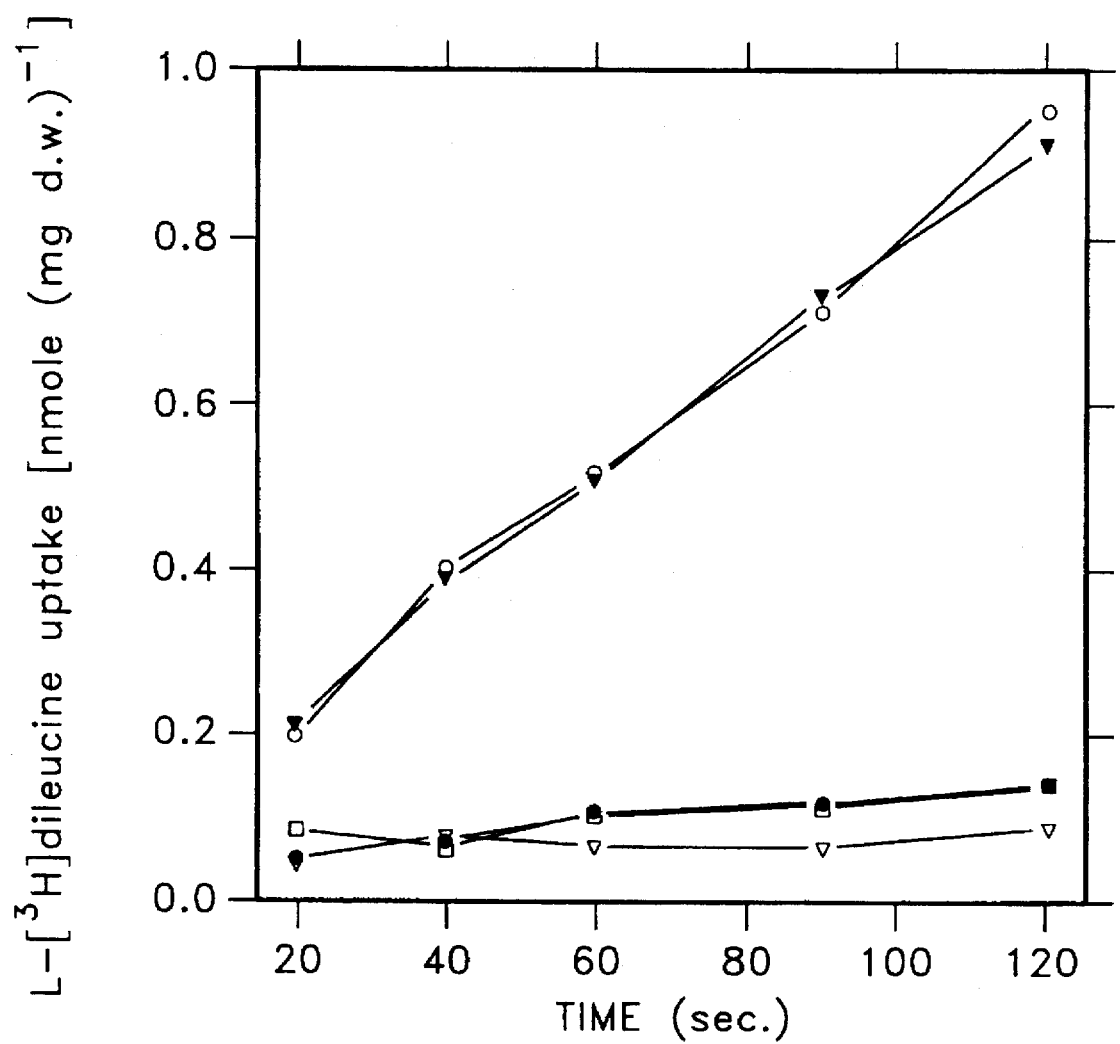
FIG. 3 shows the uptake of L-[$^3$H]dileucine by ATPTR2Ap. The Figure shows uptake by wild-type S288C, *S. cerevisiae* peptide transport mutant PB1X-9B, and PB1X-9B transformed with pPTF4. The competitor is 100× unlabelled dileucine. (○) S288C+dileucine; (●) PB1X-9B; (open ▽) PB1X-9B[pPTF4]; (solid ▽) PB1X-9B[pPTF4]+dileucine.

I. The Peptide Transport Gene of the Present Invention

The present invention arises, in part, from the exploitation of the *S. cerevisiae* peptide transport (PTR) system. In the yeast system, peptides are transported with little amino acid side-chain specificity but with strong stereospecificity for L-amino acids. Transport is under nitrogen repression control and can be induced by micromolar amounts of amino acids (Becker, J. M. et al., In: *Microorganisms and Nitrogen Sources*, Payne, J. W. (ed.), John Wiley and Sons, Inc., pp. 257–279 (1980); Island, M. D. et al., *J. Bacteriol.* 169:2132–2136 (1987)). At least three genes (designated ptr1, ptr2 and ptr3) are known to be involved in this process (Island, M. D. et al., *Curr. Genet.* 20:457–463 (1991)). Although *S. cerevisiae* strains that carry mutations in PTR1 and PTR2 are completely deficient for peptide transport (as defined by their resistance to toxic dipeptides and lack of uptake of radiolabeled peptide substrates), such mutations exhibit a substantial reversion frequency. This reversion frequency complicates their use.

Thus, one aspect of the present invention is the construction of a stable *S. cerevisiae* ptr2 mutant. Methods for isolating such mutants are described below, and by Perry, J. R. et al. (In: "Isolation and Characterization of a *Saccharomyces cerevisiae* Peptide Transport Gene," *Molecular and Cellular Biology*, volume 14 (1994), herein incorporated by reference in its entirety). Polynucleotides that encode the peptide transport genes of higher plants have been identified and isolated by their capacity to complement the peptide transport deficiency of the stable *S. cerevisiae* ptr2 strain. The nucleotide sequences of two such polynucleotides isolated from *Arabidopsis thaliana* are described herein in SEQ ID NO:1 and SEQ. ID NO:3.

The present invention relates in part to the isolation of a novel polynucleotide that is capable of hybridizing to, or recombining with, a plant gene that encodes a peptide transport protein. The polynucleotides of the present invention are "substantially" purified," in that they have been purified from undesired plant genes with which they are associated in nature. The molecules may be in either a double-stranded or single-stranded form. Such polynucleotides are capable of augmenting the transport capacity of a recipient plant, and thus may be used to facilitate the delivery of desired compounds to the plant. In an alternative embodiment, the polynucleotides of the present invention can be used to disrupt or otherwise inactivate endogenous transport systems. Such disruption renders the plant incapable of transporting toxic peptides, and thus resistant to pathogens that produce such peptides.

The capacity of the polynucleotides of the present invention to hybridize to a plant gene arises out of the extent of homology between the respective sequences of the polynucleotides. As used herein, a polynucleotide of the present invention is said to be able to "hybridize" to a plant gene if the two molecules are capable of forming an anti-parallel, double-stranded nucleic acid structure. The molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Such conventional stringency conditions are described by Sambrook, J., et al., (In: *Molecular Cloning, a Laboratory Manual*, 2nd Edition, Cold Spring Harbor Press, Cold Spring Harbor, N.Y. (1989)), and by Haymes, B. D., et al. (In: *Nucleic Acid Hybridization, A Practical Approach*, IRL Press, Washington, D.C. (1985)), both herein incorporated by reference).

Complementary molecules thus need not exhibit "complete complementarity," but need only be sufficiently complementary in sequence to be able to form a stable double-stranded structure. Departures from complete complementarity are therefore permissible, so long as such departures do not completely preclude the capacity of the molecules to form a double-stranded structure. In contrast, where two nucleic acid molecules exhibit "complete complementarity," every nucleotide of one of the molecules is complementary to a nucleotide of the other; such molecules need not have the same lengths.

The capacity of the polynucleotides of the present invention to recombine with a plant gene is determined by the extent of sequence "homology" between the polynucleotide and the plant gene. Homologous recombination is a well-studied natural cellular process which involves the exchanges of a region of one polynucleotide with a region of another (see, Sedivy, J. M., *Bio-Technol.* 6:1192–1196 (1988)). Sufficient homology for recombination requires only minimal homology in regions of the polynucleotide that flank the portion of the polynucleotide that undergoes recombination. The region may be of any length from a single base to a substantial fragment of a chromosome. Generally, a region having a length of about ten nucleotide residues is sufficient. Recombination is catalyzed by enzymes which are naturally present in both prokaryotic and eukaryotic cells.

The polynucleotides of the present invention comprise isolated nucleic acid molecules that can complement a peptide transport deficiency of *S. cerevisiae*. The term "polynucleotide" encompasses nucleic acid molecules that encode a complete protein, as well as nucleic acid molecules that encode fragments of a complete protein. The polynucleotides may comprise the wild-type allele (or a portion of such allele) of a functional peptide transport gene, or they may comprise mutated or disrupted (as by the insertion of additional DNA or RNA) alleles of such genes. As used, herein a "fragment" of a polynucleotide is an oligonucleotide whose nucleotide sequence is identical to that of a region of the polynucleotide, and whose length is greater than about 15 nucleotide residues, and preferably greater than about 20 nucleotide residues. The above-identified polynucleotides of *Arabidopsis thaliana*, SEQ. ID NO:1 and SEQ. ID NO:3, and fragments thereof comprise the preferred polynucleotides thereof.

The isolation and cloning of polynucleotides that encode *Arabidopsis thaliana* peptide transport proteins permits the isolation of analogous, complementary polynucleotides from other plants. The functional role of such isolated polynucleotides can be readily determined by transforming them into the above-described stable peptide transport-deficient yeast strain, and evaluating whether transformants acquire the capacity to transport intact peptides. Thus, the methods of the present invention permit the isolation of polynucleotides from other plant species. Such polynucleotides are the equivalents of the preferred polynucleotides of the present invention.

In one embodiment of the invention, the polynucleotides will be operably linked to regulatory sequences sufficient to permit the polynucleotide's transcription. Such polynucleotides may be incorporated into nucleic acid vectors that are sufficient to permit either the propagation or maintenance of the polynucleotide within a host cell. The nature of the regulatory elements will depend upon the host cell, and the desired manner of expressing the polynucleotide. Examples of suitable regulatory elements include constitutive or inducible prokaryotic promoters, such as the λpL or pR promoters, or other well-characterized promoters (e.g., lac, gal, trp, ara, hut, etc.). Other promoters which may be employed are the nos, ocs and CaMv promoters. Efficient plant promoters that may be used are over-producing plant promoters such as the small subunit (ss) of the ribulose 1, 5 biphosphate carboxylase from soybean (Berry-Lowe, et al., *J. Molec. App. Gen.* 1:483–498 (1982)) and the promoter of the chlorophyll a/b binding protein. These two promoters are known to be light induced in eukaryotic plant cells (see *Genetic Engineering of Plants, An Agricultural Perspective,*" Cashmore, A. (ed), Plenum, N.Y., pp. 29–38 (1983); Coruzzi, G. et al., *J. Biol. Chem.* 258:1399 (1983); and Dunsmeier, P. et al., *J. Molec. App. Gen.* 2:285 (1983)). The 35S promoter is particularly preferred.

Preferred prokaryotic vectors include plasmids such as those capable of replication in *E. coil* such as, for example, pBR322, ColE1, pSC101, pACYC 184, πVX. Such plasmids are, for example, disclosed by Maniatis, T., et al. (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, N.Y. (1982), pp. 307–329). Suitable Streptomyces plasmids include plJ101 (Kendall, K. J., et al., *J. Bacteriol.* 169:4177–4183 (1987)), and *Streptomyces* bacteriophages such as øC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al.

(Rev. Infect. Dis. 8:693–704 (1986)), and Izaki, K. (Jpn. J. Bacteriol. 33:729–742 (1978)).

Examples of suitable yeast vectors include the yeast 2-micron circle, the expression plasmids YEP13, YCP and YRP, etc., or their derivatives. Such plasmids are well known in the art (Botstein, D., et al., *Miami Wntr. Syrup.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Sherman, F. et al., In: *Methods in Yeast Genetics*, Cold Spring Harbor Laboratory, Cold Spring Harbor, N.Y. (1986)).

As indicated, the invention particularly contemplates providing the polynucleotides of the present invention to plants, especially tobacco, coffee, wheat and other cereals, apple and other non-citrus fruit producers, and citrus fruit crops. Suitable plants include, for example, species from the genera Fragaria, Lotus, Medicago, Onobrychis, Trifolium, Trigonefla, Vigna, Citrus, Linum, Geranium, Manicot, Daucus, Arabidopsis, Brassica, Raphanus, Sinapis, A tropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicurn, Pennisetum, Ranunculus, Senecio, Salpiglossis, Cucumis, Browallia, Glycine, Lolium, Zea, Triticum, Sorghum, Ipomoea, Passiflora, Cyclamen, Malus, Prunus, Rosa, Rubus, Populus, Santalure, Allium, Lilium, Narcissus, Ananas, Arachis, Phaseolus, Pisum and Datura.

In one embodiment, such polynucleotides will be provided without promoters or other regulatory elements, but under conditions sufficient to permit the polynucleotide to recombine with and replace a region of the endogenous plant peptide transport gene. In an alternative embodiment, the polynucleotides will be administered to the plant operably linked to regulatory elements and/or vector elements.

Any of a variety of methods may be used to introduce the polynucleotides of the present invention into a plant cell. The genetic material can be microinjected directly into the plant embryo cells or introduced by electroporation as described in Fromm et al., *"Expression of Genes Transformed into Monocot and Dicot Plant Cells by Electroporation,"* Proc. Nat'l. Acad. Sci. U.S.A. 82:5824–28 (1985) or it can be introduced by direct precipitation using polyethylene glycol as described in Paszkowski et al., *EMBO J.* 3:2717–22 (1984). In the case of monocotyledonous plants, pollen may be transformed with total DNA or an appropriate functional clone providing resistance, and the pollen then used to produce progeny by sexual reproduction.

The Ti plasmid of *Agrobacterium tumefaciens* provides a means for introducing DNA into plant cells (Caplan, A., et al., *Science* 815–821 (1983); Schell, J. et al., *Bio/Technology*, April 1983, pp. 175–1980; Fraley, R. T., et al., Proc. Nat'l. Acad. Sci. U.S.A. 80:4803 (1983); (Hooykass, P. J. J. et al., In: *Molecular Form and Function of the Plant Genome*, Vlotan-Doltan, L. et al. (eds.), Plenum Press, N.Y., pp. 655–667 (1984); Horsch, R. B. et al., In: *Current Communications in Molecular Biology*, Cold Spring Harbor Press, Cold Spring Harbor, N.Y., pp. 13–19 (1988); Horsch et al., *Science* 233:496–498 (1984); all herein incorporated by reference). As such, it provides a highly preferred method for introducing the polynucleotides of the present invention into plant cells Ti plasmids contain two regions essential for the production of transformed cells. One of these, termed "transfer DNA" (T DNA), induces tumor formation. The other, termed "virulent region," is essential for the formation but not maintenance of tumors. It is possible to insert the polynucleotides of the present invention into the T DNA region without affecting its transfer function. By removing the tumor-causing genes so that they no longer interfere, the modified Ti plasmid can then be used as a vector for the transfer of the gene constructs of the invention into an appropriate plant cell. The polynucleotides of the present invention are preferably inserted between the terminal sequences that flank the T-DNA.

A particularly useful Ti plasmid vector is pGV3850, a non-oncogenic derivative of the nopaline Ti plasmid C58 (Caplan, A., et al., *Science* 815–821 (1983)). This vector utilizes the natural transfer properties of the Ti plasmid. The internal T DNA genes that determine the undifferentiated crown gall phenotype have been deleted and are replaced by any commonly used cloning vehicle (such as pBR322). The cloning vehicle sequence contained between T DNA border regions serves as a region of homology for recombination to reintroduce foreign DNA cloned in a derivative of the same cloning vehicle. Any polynucleotide of the present invention cloned in such plasmid can thus be inserted into pGV3850 by a single recombination of the homologous sequences. Antibiotic resistance markers can be added to the plasmid to select for the recombination event. The presence of the nopaline synthase (nos) gene in pGV3850 facilitates the monitoring of the transformation.

The introduction of the Ti plasmid is typically accomplished by infecting a wounded leaf of the plant with *Agrobacterium tumefaciens* bacteria that contains the plasmid. Under appropriate growth conditions, a ring of calli forms around the wound (Hooykass, P. J. J. et al., In: *Molecular Form and Function of the Plant Genome*, Vlotan-Doltan, L. et al. (eds.), Plenum Press, N.Y., pp. 655–667 (1984)). The calli are then transferred to growth medium, allowed to form shoots, roots and develop further into plants.

The procedure can alternatively be performed in tissue culture. All plants from which protoplasts can be isolated and cultured to give whole regenerated plants can be transformed by the present invention so that whole plants are recovered which contain the introduced polynucleotide. There is an increasing body of evidence that practically all plants can be regenerated from cultured cells or tissues, including but not limited to all major cereal crop species, sugarcane, sugar beet, cotton, fruit and other trees, legumes and vegetables (Hooykass, P. J. J. et al., In: *Molecular Form and Function of the Plant Genome*, Vlotan-Doltan, L. et al. (eds.), Plenum Press, N.Y., pp. 655–667 (1984); Horsch, R. B. et al., In: *Current Communications in Molecular Biology*, Cold Spring Harbor Press, Cold Spring Harbor, N.Y., pp. 13–19 (1988)). Methods for regenerating plants from cultural protoplasts are described by Evans et al. (*Handbook of Plant Cell Culture* 1:124–176; by Davey, M. R., In: *Protoplasts 1983—Lecture Proceedings*, pp. 19–29, Birkhauser, Basel (1983)); Dale, P. J. (In: *Protoplasts 1983—Lecture Proceedings*, pp. 31–41, Birkhauser, Basel (1983)); Binding, H. (In: *Plant Protoplasts*, CRC Press, Boca Raton, pp. 21–37 (1985)) and Cooking, E. C. In: *Molecular Form and Function of the Plant Genome*, Vlotan-Doltan, L. et al. (eds.), Plenum Press, N.Y., pp. 27–32 (1984)).

Regeneration efficiency varies from species to species of plants, but generally a suspension of transformed protoplasts containing the introduced gene sequence is formed. Embryo formation can then be induced from the protoplast suspensions, to the stage of ripening and germination as natural embryos. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

Other systems, such as cauliflower mosaic virus, CaMV (Hohn, B., et al., In "*Molecular Biology of Plant Tumors*," Academic Press, New York, pp. 549–560; and Howell, U.S. Pat. No. 4,407,956) can also be used to introduce the polynucleotides of the present invention into plant cells. In accordance with such methods, the entire CaMV viral DNA genome is inserted into a parent bacterial plasmid thus creating a recombinant DNA molecule which can be propagated in bacteria. After cloning, the recombinant plasmid is cleaved with restriction enzymes either at random or at unique sites in the viral portion of the recombinant plasmid for insertion of the polynucleotides of the present invention. The modified viral portion of the recombinant plasmid is then excised from the parent bacterial plasmid, and used to inoculate the plant cells or plants.

After transformation of the plant cell or plant, the same may be selected by aid of an appropriate marker, such as antibiotic resistance, and then assessed to determine whether it contains the desired polynucleotide of the invention. The mature plants, grown from the transformed plant cells, can be selfed to produce an inbred plant whose seeds will contain the introduced polynucleotides of the present invention. These seeds can be grown to produce plants that exhibit any of a set of desired properties.

In one embodiment of the present invention, the exhibited property will be an increased facility to transport peptides. In this embodiment, the polynucleotides of the invention are provided to the plant or plant cells along with transcriptional regulatory sequences, such that an overexpression of the plant's peptide transport gene occurs. Such plants are desirable in that their enhanced peptide transport system can be used to facilitate the up take of peptide-associated molecules.

In an alternative embodiment, the exhibited property will be an impairment or obliteration of the plant's peptide transport system. Such plants are produced by providing cells with mutated polynucleotides and permitting such polynucleotides to recombine with, and mutate, the cells' endogenous peptide transport gene. As a consequence of such recombination, the plant will have lost the capacity to mediate peptide transport. Such plants, and their fruit, are valuable in that they are resistant to the toxic peptides produced by plant pathogens.

Parts obtained from the regenerated plant, such as flowers, seeds, leaves, branches, bark, fruit, and the like are covered by the invention. Progeny and variants, and mutants of the regenerated plants are also included within the scope of this invention.

II. Uses of the Peptide Transport Gene of the Present Invention

A. Resistance to Plant Pathogens and Herbicides

Several plant pathogens have been found to attack plants through the production of toxic peptides. For example, phaseotoxin, produced by *Pseudomonas syringae* pv. *phaseolicola*, the causal agent of halo blight of bean, is a tripeptide that is further processed by peptidases in vivo to a smaller active form (Willis, D. K. et al., *Experimentia* 47:765–771 (1991); Gross, D. C., *Ann. Rev. Phytopathol.* 29:247–278 (1991)). Likewise, tabtoxin, produced by *Pseudomonas syringae* pv. *tabaci*, is the causal agent of wildfire of tobacco. Many phytopathogenic fungi produce toxic peptides (Higgins, C. F. et al., In: *Encyclopedia of Plant Phsyiology, N. S.*, volume 14A, Boulter, D. et al. (eds.) Springer, N.Y., pp. 438–458 (1982)). Such resistance can be manifested by hardier plants, or by foodstuffs (fruit, leaves, etc.) that are more resistant to spoilage or decay.

Substantial evidence suggests that the uptake of toxic peptides is mediated by peptide transport systems (McCarthy, P. J. et al., *Antimicrob. Agents Chemother.* 28:494–499 (1985); McCarthy, P. J. et al., *J. Gen. Micro.* 131:775–780 (1985); Moneton, P. et al., *J. Gen. Micro.* 132:2147–2153 (1986); Yadan, J. C. et al., *J. Bacteriol.* 160:884–888 (1984)); Payne, J. W. et al., *FEMS Microbiol. Letts.* 28:55–60 (1985); Mehta, R. J. et al., *Antimicrob. Agents Chemother.* 25:373–374 (1984)). Since the polynucleotides of the present invention define the genetic loci responsible for peptide transport such polynucleotides can be used to produce plants that lack functional peptide transport systems. Such plants would be unable to transport such conjugated peptides and hence would be resistant to such pathogens.

In this regard, the present invention provides a method for conjugating an antimicrobial or antifungal agent or a pesticide to a peptide in order to provide a more effective treatment against such pathogens. In a similar manner, toxic peptide derivatives may be used as herbicides to eliminate undesired peptide transport proficient plants (such as weeds, etc.) that would otherwise compete with peptide transport deficient plants for soil nutrients.

Examples of toxic peptide or peptidyl molecules that may be used as antimicrobial, herbiciadal, or pesticidal agents include:

(A) metabolic toxins (such as the antifungal agent FMDP [$N^3$-(4-methoxyfumaroyl)-L-2,3 diaminopropanoic acid), toxic nucleotides (such as halogenated nucleotides (e.g., 5-fluoroorotic acid), dideoxynucleotides, mutagenic nucleotide or nucleoside analogs, etc. (Kingsbury, W. D. et al., *J. Med. Chem.* 27:1447–1451 (1984); Andruszkiewicz, R. et al., *J. Med. Chem.* 30:1715–1719 (1987); Andruszkiewicz, R. et al., *J. Med. Chem.* 33:132–135 (1990); Andruszkiewicz, R. et al., *J. Med. Chem.* 33:2755–2759 (1990); Milewski, S. et al., *J. Drugs Expt. Clin. Res.* 14:461–465 (1988));

(B) peptides that contain toxic amino acids (such as oxalysine, fluorophenylalanine, ethionine, unusual D amino acids, etc.) (McCarthy, P. J. et al., *Antimicrob. Agents Chemother.* 28:494–499 (1985); Marder, R. et al., *J. Bacteriol.* 36:1174–1177 (1978); Moneton, P. et al., *J. Gen. Micro.* 132:2147–2153 (1986); Mehta, R. J. et al., *Antimicrob. Agents Chemother.* 25:373–374 (1984); Bosrai, M. et al., *J. Gen. Microbiol.* 138:2353–2362 (1992));

(C) toxic peptides and peptidyl molecules such as bacilysin (Milewski, S. et al., *Arch. Microbiol.* 135:130–136 (1983); Moneton, P. et al., *J. Gen. Microbiol.* 132:2147–2153 (1986); Kenig, M. et al. *J. Gen. Microbiol.* 94:37–45 (1976)), polyoxins (especially polyoxin D) (Becker, J. M. et al., *Antimicrob. Agents Chemother.* 23:926–929 (1983)), nikkomycins (especially nikkomycin Z) (Dahn, U. et al., *Arch. Microbiol.* 107:143–160 (1976)), and their analogs (Smith, H. A. et al., *Antimicrob. Agents Chemother.* 29:33–39 (1986); Naider, F. et al., *Antimicrob. Agents Chemother.* 24:787–796 (1983); Krainer, E. et al., *J. Med. Chem.* 34:174–180 (1991); Shenbagamurthi. P. et al., *J. Med. Chem.* 26:1518–1522 (1983); Shenbagamurthi. P. et al., *J. Med. Chem.* 29:802–809 (1986); Khare, R. K. et al., *J. Med. Chem.* 83:650–656 (1988); Emmer, G. et al., *J. Med. Chem.* 28:278–281 (1985); Decker, H. et al., *J. Gen Microbiol.* 137:1805–1813 (1991); Delzer, J. et al., *J. Antibiot.* 37:80–82 (1984); all herein incorporated by reference).

In a preferred embodiment, the peptides of such conjugates will be N-α-acetylated, since such modification facilitates the uptake of peptide molecules.

The impairment of the native capacity of the host plant to mediate peptide transport may be impaired in any of a variety of ways. In one embodiment, such impairment may be accomplished by mutating the normal, functional (i.e. "wild-type") endogenous allele of a plant cell's peptide transport gene. Such mutagenesis may be accomplished by subjecting seedlings to mutagenic agents, such radiant energy (e.g., ultra-violet light, X-rays, etc.) or chemical mutagens. Suitable chemical mutagens include base analogs (such as, 5-bromouracil, or 2-aminopurine); deaminating agents (such as, for example, nitrous acid, hydroxylamine); alkylating agents (such as, for example, methyl methane sulfonate, ethyl methane sulfonate nitrosoguanidine); intercalating agents (such as, for example, acridine orange, ethidium bromide, psoralen.), and other mutagens. Techniques for mutagenizing nucleic acid molecules may be found in Miller, J. H. (In: *Experiments in Molecular Biology*, Cold Spring Harbor Laboratory, Cold Spring Harbor, N.Y. (1972)), and Silhavy, T. J., et al. (In: *Experiments with Gene Fusions*, Cold Spring Harbor Laboratory, Cold Spring Harbor, N.Y. (1984)).

It is possible that methods of site-directed mutagenesis (Itakura, K., et al., *Ann. Rev. Biochem.* 53:323–356 (1984), Adelman et al., *DNA* 2:183 (1983) and Crea et al., *Proc. Natl. Acad. Sci. (U.S.A.)* 75:5765 (1978)) may be expanded to permit the use of vectors to create predefined mutations in the peptide transport polynucleotides. Such mutated molecules could then be introduced into a plant cell and permitted to recombine with the cell's endogenous peptide transport gene, to thereby produce a peptide transport deficient plant cell.

The successful mutation of the endogenous gene can be readily determined by evaluating the capacity of the cell or plant to take up peptides. Methods for performing such determinations are presented below. Alternatively, the cloned polynucleotide sequences can be used as probes to determine the extent of cellular transcription of the endogenous peptide transport gene.

In yet another embodiment, the sequences of the polynucleotides of the present invention can be used to define "antisense oligonucleotides" that can repress the transcription or translation of a functional endogenous peptide transport gene. Such antisense molecules can be provided to the plant via a vector, such as a CaMV vector, that expresses the antisense molecule, using a promoter such as the 35S promoter. In general, an "antisense oligonucleotide" is a nucleic acid (either DNA or RNA) whose sequence is sufficiently complementary to the sequence of a target mRNA molecule (or its corresponding gene) that it is capable of binding to, or hybridizing with, the mRNA molecule (or the gene), and thereby impairing (i.e. attenuating or preventing) the translation of the mRNA molecule into a gene product. To act as an antisense oligonucleotide, the nucleic acid molecule must be capable of binding to or hybridizing with that portion of target mRNA molecule (or gene) which mediates the translation of the target mRNA. Thus, antisense molecules of the present invention are capable of binding to an endogenous peptide transport gene or mRNA and inhibiting its activity. Antisense oligonucleotides are disclosed in European Patent Application Publication Nos. 263,740; 335,451; and 329,882, and in PCT Publication No. WO90/00624, all of which references are incorporated herein by reference.

One manner in which an antisense oligonucleotide may achieve these goals is by having a sequence complementary to that of the translation initiation region of the target mRNA molecule. The size of such an oligomer can be any length that is effective for this purpose. Preferably, the antisense oligonucleotide will be about 10–30 nucleotides in length, most preferably, about 15–24 nucleotides in length.

Alternatively, one may use antisense oligonucleotides that are of a length that is too short to be capable of stably hybridizing to an mRNA molecule under physiological, in vivo conditions. Such an oligonucleotide may be from about 6–10, or more nucleotides in length. To be used in accordance with the present invention, such an oligonucleotide is preferably modified to permit it to bind to a locus of the translation region of the target mRNA. Examples of such modified molecules include oligonucleotides bound to an antibody (or antibody fragment), or other ligand (such as a divalent crosslinking agent (such as, for example, trimethylpsoralin, 8-methoxypsoralin, etc.) capable of binding to a single-stranded mRNA molecules.

In yet another embodiment, ribozymes can be employed as inhibitors of the endogenous peptide transport gene. Ribozymes (RNA enzymes) are catalytic RNA molecules that can cleave RNA target molecules with which they hybridize (Cech, T. et al., *Cell* 27:487 (1981); Cech, T., *Science* 256:1532–1539 (1987); Cech, T. et al., *Ann. Rev. Biochem.* 55:599–630 (1986); James, W., *Antivir. Chem. Chemother.* 2: 191–214 (1991)).

An artificial ribozyme can be designed to specifically cleave a target RNA by flanking sequences complementary to the target (Haseloff, J. et al., *Nature* 334:585–591 (1988); Cameron, F. et al., *Proc. Natl. Acad. Sci. U.S.A.* 86: 9139–9143 (1989); James, W., *Antiviral Chemistry & Chemotherapy* 2: 191–214 (1991). The minimum requirement for cleavage within the target RNA is the location of a suitable three base sequence GUC, GUA, or GUU preceding the cleavage site. Artificial ribozymes having a characteristic "hammerhead" secondary structure have been designed by Haseloff, J. et al. (*Nature* 334:585–591 (1988); Jeffries, A. et al., *Nucleic Acids Res.* 17:1371–1377 (1989); Gerlach et al. WO Patent No. 8905852 (1989); Goodchild, J. et al., *Arch. Biochem. Biophys.* 254:386–391 (1991); James, W., *Antivir. Chem. Chemother.* 2: 191–214 (1991)).

B. Targeted Delivery of Desired Affector Compounds

The capacity to control the extent of expression of plant peptide transport genes provides a means for facilitating the delivery of desired compounds into plant cells. Such desired compounds are "affectors of a plant characteristic" if they confer or cause a detectable change in a plant trait. Such characteristics include size, growth rate, resistance to pathogens or herbicides, color scent, nutritional value, sensitivity to cold or heat, sensitivity to drought or overwatering. The affectors of such characteristics may be nucleotides, polynucleotides, auxins, organic molecules (including proteins, peptides, pigments, perfumes), etc. A capacity to augment the cellular ability to incorporate desired peptides can be used to produce superior or more nutritious foods (Adibi, S., *Metab.* 36:1001–1011 (1987)). Similarly, such a capacity can facilitate the uptake of non-peptide affectors that have been conjugated or associated with a peptide, such that the affector is delivered into the plant in conjunction with the peptide (Higgins, C., *Nature* 327:655–656 (1987)). For example, chromogenic affectors may be conjugated to peptides in order to produce flowers having more desired coloration. Alternatively, the peptides may be conjugated to auxin affectors (such as gibberelin, indoleacetic acid, etc.) in order to facilitate plant growth and/or development.

The extent of expression can be controlled by providing the plant's cells with vectors that contain multiple copies of the peptide transport polynucleotides. Alternatively, such vectors may contain efficient (and/or inducible) promoters that are operably linked to the polynucleotide, and which can therefore mediate its transcription at an elevated rate.

In an alternative embodiment, the polynucleotides of the present invention may be joined to high efficiency promoters, and then introduced into the plant cell under conditions sufficient to recombine with the endogenous gene. Such action will result in the replacement of the endogenous promoter with a high efficiency promoter.

In lieu of altering the transcriptional regulation of the peptide transport gene, the methods of the present invention permit one to mutate the cloned polynucleotides in order to produce a polynucleotide that encodes a more active (or otherwise more desirable) peptide transport gene. Such desired variant genes can be readily evaluated by determining the transport capacity of yeast cells containing such variant polynucleotides, or by using the polynucleotides of the present invention as probes of mRNA transcription.

Having now generally described the invention, the same will be more readily understood through reference to the following examples which are provided by way of illustration, and are not intended to be limiting of the present invention.

EXAMPLE 1

Isolation of *S. cerevisiae* Mutants Carrying Mutations in their Peptide Transport System As a means for cloning a plant peptide transport gene, the gene that controls peptide transport in *S. cerevisiae* was cloned. The isolation of this gene permitted the construction of a stable, transport-deficient yeast strain.

The ptr2 gene of *S. cerevisiae* was isolated by functional complementation of the dipeptide transport-deficient (ptr2⁻) phenotype. Yeast strain PB1X-9B (MATα ura3-52 leu2-3 lys1-1 his4-38 ptr2-2) was transformed with a YCp50-based *S. cerevisiae* genomic DNA library obtained from the American Type Culture Collection (Rose, M. D. et al., *Gene* 29:113–124 (1984)) (ATCC 37415). To prepare the library, bacterial cells were resuspended in 5 ml of LB broth and plated on LB plates containing 50 µg of ampicillin per ml. Approximately 10,000 clones were harvested, and the plasmid DNA was isolated by the alkaline lysis method (Sambrook, J. et al., In: *Molecular Cloning A Laboratory Manual*, Cold Spring Harbor Laboratory, Cold Spring Harbor, N.Y. (1989)). pZ523 columns were used to remove contaminating chromosomal DNA (Zervos, P. H. et al., *Biotechniques* 6:238–242 (1988)).

Yeast strains were transformed by the LiCl method (Ito, H. et al., *J. Bacteriol.* 153:163–168 (1983)). The cells were then plated on solid minimal medium (MM) supplemented with 1.3 mM L-histidine and 10 mM L-lysyl-L-leucine. The histidine served to induce the peptide transport system and to meet the auxotropic requirement conferred by the his4-38 mutation present in the host strain. L-Lysyl-L-leucine served as a source of lysine and leucine in those yeast transformants capable of transporting the dipeptide. Two yeast transformants, designated PB1X-9B(pJP1) and PB1X-9B (pJP2), were recovered after incubation at 30° C. for 5 days.

Whole-cell DNA, isolated from both primary yeast transformants and the transforming plasmids, was subsequently amplified and recovered in *E. coli* HB101. Plasmid DNA was isolated from the resulting bacterial transformants and partially characterized with restriction enzymes. Both plasmids, pJP1 and pJP2, yielded identical restriction patterns when digested with PstI and BamHI. The ptr2 gene encodes a 602 amino acid hydrophobic polypeptide with 12 putative hydrophobic segments. The protein demonstrates all the previously identified characteristics of peptide transport in yeast. A data base search indicated the yeast peptide transporter may be the second protein discovered in a new class of membrane bound proteins (Tsay, Y-F. et al., *Cell* 72:705–713 (1993). The nucleotide sequence of the yeast ptr gene, and the deduced amino acid sequence of the protein is provided by Perry, J. R. et al. (In: "Isolation and Characterization of a *Saccharomyces cerevisiae* Peptide Transport Gene," *Molecular and Cellular Biology*, volume 14 (1994), herein incorporated by reference).

Plasmid pJP2 was then reintroduced into PB1X-9B. The resulting secondary yeast transformants were tested for the ability to use a variety of dipeptides as sources of amino acids and for sensitivity to the toxic dipeptide L-alanyl-L-ethionine. Thus, strains were grown in YEPG broth at 30° C. to a titer of $10^8$ cells per ml. The cells were harvested by centrifugation, washed twice with sterile water and resuspended at $1.0 \times 10^7$ cells per ml. A 5-µl aliquot was applied to solid MM containing dipeptides and amino acids as required. Four types of solid media were routinely used in assessing dipeptide utilization: MM+L-leucyl-L-leucine-L-lysine+L-histidine, MM-L-lysl-L-lysine-L-leucine-L-histidine, MM-L-lysl-L-leucine-L-histidine, and MM-L-histydyl-L-leucine-L-lysine. All dipeptides were present at a concentration of 80 µM, while amino acids and nucleotide bases were added as required at standard concentrations (Sherman, F. et al., In: *Methods in Yeast Genetics*, Cold Spring Harbor Laboratory, Clod Spring Harbor, N.Y. (1986)). The plates were incubated at 30° C. for 48 hours and then scored for growth. The secondary yeast transformants were able to utilize all dipeptides tested as sources of amino acids and were sensitive to the growth-inhibiting effects of L-alanyl-L-ethionine. In addition, PB1X-9B(pJP2) was able to transport radiolabeled dileucine at levels approximating those of the wild type, while the control strain PB1X-9B (YCp50), failed to accumulate the radiolabeled substrate. These results showed that the transformant had the expected wild-type phenotype and that the ptr2-2-complementing activity was plasmid-associated and not due to a reversion event at the ptr2 locus.

In order to form a more stable yeast ptr mutant, a one step method (Orr-Weaver, T. L. et al., *Methods Enzymol.* 101:228–245 (1983)) was used to cause the chromosomal disruption of the ptr gene of a non-mutant yeast strain. A 2.0-kb DNA fragment carrying the LEU2 gene of *S. cerevisiae* BamHI-HindIII DNA fragment from plasmid p J J283 (Jones, J. S. et al., *Yeast* 6:363–366 (1990)). The fragment was isolated from an agarose gel treated with T4 DNA polymerase, and then blunt-end ligated into a 653-bp deleted region of the PTR2 protein coding region of plasmid pJP15 was constructed by cloning a 1.64-kbp BamHI-EcoRI DNA fragment from plasmid pJP9 into plasmid pRS3062. This 1.65-kbp fragment contained a DNA sequence that includes 495 bp of the promoter region and 1,147 bp of the protein coding region of the ptr2 gene. Plasmid pRS3062 is a derivative of plasmid PRS306 (Sikorski, R. S. et al., *Genetics* 122:19–27 (1989)) in which a unique AatII restriction endonuclease site had been removed by the digestion with AatII, treatment with T4 DNA polymerase, and religation. The deleted region of plasmid PJ15 was generated by restriction endonuclease digestion with AatII and MscI, resulting in the excision of a 653-bp region that is contaminated within the PTR2 protein coding region. The ends of the deleted pJP15 molecule were made blunt with T4 DNA polymerase and ligated with the blunt-ended LEU2 DNA fragment. The resulting plasmid, pJP23(Cowan, S. W. et al., Nature 358:727–733 (1992)) was recovered in E. coli, and the structure was confirmed by restriction endonuclease analysis. Plasmid PJP23 contains the LEU2 gene oriented so that the direction of transcription opposes that of ptr2. A 2.6-kbp NdeI-DraI DNA fragment containing the inserted LEU2 gene flanked by ptr2 DNA sequences was excised and used as a substrate in transforming the ptr2$^+$ strain PB 1 X-2A.

Leu$^+$ yeast transformants were selected on MM medium supplemented with uracil, L-lysine, and L-histidine. The resulting leu$^+$ yeast transformants were patched onto fresh medium and then tested for the ability to use L-lysyl-L-leucine as a source of lysine in growth experiments and for sensitivity to L-alanyl-L-ethionine in disk assays. A single yeast transformant displaying the leu$^+$ ptr$^-$ phenotype, designated PB1X2AΔ was considered for further characterization. The integration event at the ptr2 locus was confirmed by Southern transfer hybridization analysis.

EXAMPLE 2

Isolation of Arabidopsis thaliana cDNAs Capable of Complementing S. cerevisiae PTR Mutants The isolation of plant genes responsible for peptide transport was accomplished by preparing cDNA from the grass, Arabidopsis thailiana, and then determining whether that cDNA was capable of complementing the PTR deficiency of the above-described yeast mutants.

An Arabidopsis thaliana cDNA library was obtained from Minet, F. et al. (Centre National de la Recherche Scientifique, Gif sur Yvette, France). The cDNA of the library was prepared from the mRNA of complete young seedlings (stage II leaves) including roots of Arabidopsis thaliana (L). Heynh (Landsberg erecta ecotype). The cDNAs were ligated to CACA adapters and then inserted into BstXI sites flanked by NotI sites in the yeast/E. coli expression vector pFL61 (Minet, M. et al., Plant J. 2:417–422 (1992)). Expression in yeast is controlled by the phosphoglycerate kinase (PGK) promoter.

For amplification and storage, the library was maintained in E. coli strain DH5α (supE44 hsdR17 recA1 gyrA96 thi-1 relA1). Yeast hosts used were S288C (MATα SUC2 mal mel gal2 CUP1), PB1X-9B (MATα ura3-52 leu2-3,112 lys1-1 his4-38 ptr2-2), PB1X-2A (MATα ura3-52 leu 2-3, 112 lys1-1 his4-38 ptr2-2), and PB1X-2AΔ (MATα ura3-52 leu2-3, 112 lys1-1 his4-38 ptr2::leu2). All yeast strains, except PB1X-2AΔ, were constructed using the methods described by Sherman, F. et al., In: Methods in Yeast Genetics, Cold Spring Harbor Laboratory, Clod Spring Harbor, N.Y. (1986), and by Perry, J. R. et al. (In: "Isolation and Characterization of a Saccharomyces cerevisiae Peptide Transport Gene," Molecular and Cellular Biology, volume 14 (1994), both herein incorporated by reference). As indicated above, PB1X-2AΔ was generated from strain PB1X-2A using a one-step gene disruption/replacement strategy (Rothstein, R. J. et al., Methods Enzymol. 101:202–211 (1983)) where a 653-bp region internal to the coding region was deleted and replaced by 2.0 kb fragment containing the LEU2 gene of S. cerevisiae.

S. cerevisiae S288C, PB1X-9B, PB1X-2A, and PB1X-2AΔ were maintained on YEPD agar containing (w/v) 1% yeast extract-2% Bacto-Peptone (Difco Laboratories, Detroit Mich.) and 2% glucose. All experiments conducted with these strains were done in synthetic complete medium (SC) containing yeast nitrogen base (Difco) without amino acids and ammonium sulfate, 1 mg of allantoin per ml, 2% glucose and amino acid supplements as indicated. Amino acids were supplied as 0.15 mM unless indicated otherwise. Solid media contained 2% agar or 2% nobel agar in the case of disk assays. All yeast strains were incubated at 30° C. E. coli strain DH5α was routinely maintained on SOB medium (Sambrook, J. et al., In: Molecular Cloning A Laboratory Manual, Cold Spring Harbor Laboratory, Cold Spring Harbor, N.Y. (1989)) while transformed DH5α strains were grown on LB medium plus 100 ml ampicillin at 37° C.

The Saccharomyces cerevisiae strains PB1X-9B and PB1X-2AΔ, which carry mutations in leucine, histidine, and lysine biosynthesis as well as in peptide transport, are unable to grow on minimal medium supplemented with dipeptides containing amino acids which satisfy the auxotrophic requirements of the mutants. To isolate a plant gene which codes a peptide transporter, strains PB1X-9B and PB1X-2AΔ were transformed with the cDNA library (Gietz, D., et al., Nuc. Acid. Res 20:1425 (1992)) and transformants were selected on SC media supplemented with L-leucine, L-lysine, L-histidine (100 μM), washed from plates with sterile dH20 and selected on dipeptide media (SC plus 80 μM his-leu, and 80 μM lys-leu). A total of 21 clones were recovered (15 from PB1X-9B and 6 from PB1X-2AΔ). Colonies were reselected on solid dipeptide medium and those colonies able to grow were analyzed on drop out plates and plasmid cured to show concomitant loss of the selectable marker and peptide transport phenotypes. Plasmid DNA was isolated and reintroduced into both PB1X-9B and PB1X-2A. Plasmids able to restore the growth of the mutants on dipeptide media were recovered, purified and analyzed further.

Two clones from each group were able to restore peptide transport. NotI restriction analysis of the two PB1X-2AΔ transformants showed an identical insert of 2.0 kb (designated pDTF1 and pDTF2) and the two PB1X-9B transformants showed an identical insert of 2.8 kb (pPTF3 and pPTF4). The remaining clones showed either no insert at all or multiple bands upon restriction with NotI. The 2.0 kb transformants pDTF1 and pDTF2 did not show sensitivity to toxic peptides (discussed below) while the 2.8 kb transformants, pPTF3 and pPTF4 displayed sensitivity to all peptides tested. Plasmids pPTF3 and pPTF4 transformed into the deletion strain PB1X-2A showed identical phenotypes to that of pPTF3 and pPTF4 transformed into the PB1X-9B genetic background as judged by growth on peptides and disk assay. By southern hybridization, an α-$^{32}$P labeled probe consisting of the entire NotI 2.8 kb insert hybridized to uncut, and NotI digest pPTF3 and pPTF4 plasmid DNA but not to uncut and NotI digested pDTF1 or pDTF2 plasmid DNA. Based on these results, the 2.8 kb plasmid pPTF4 was chosen for further analysis. Plasmid pPTF4 was found to comprise cDNA for an Arabidopsis peptide transport protein.

The Arabidopsis gene carried within the 2.8 kb insert of plasmid pPTF4 was designated "atptr2a," and the protein encoded by this gene was termed "ATPTR2Ap protein." The sequence of the atptr2a cDNA is presented herein as SEQ ID NO:1; the deduced sequence of the ATPTR2Ap protein is presented herein as SEQ ID NO:2.

The Arabidopsis gene carried within the 2.0 kb insert of plasmid pDTF1 was designated "atptr2b," and the protein encoded by this gene was termed "ATPTR;2Bp protein."

The sequence of the atptr2b cDNA is presented herein as SEQ ID NO:3; the deduced sequence of the ATPTR2Bp protein is presented herein as SEQ ID NO:4:

In sum, functional complementation of yeast mutants has been used successfully to clone plant polynucleotides that are capable of complementing a yeast PTR deficiency. The method permits the rapid identification of those plant genes that are functionally homologous to yeast genes. Although functional complementation has been used to clone a number of plant transport genes including potassium ion transporters, a sucrose transporter and two amino acid permeases, its applicability requires not only well characterized yeast mutants, but also the capacity of the plant gene to function in the yeast. Thus, the applicability of the method to the cloning of a particular plant gene cannot be assessed in advance. Expression of plant genes in yeast also affords greater flexibility in analyzing the functional characteristics of the protein product.

EXAMPLE 3

Sequence Analysis of Cloned *Arabidopsis thaliana* cDNA

The nucleotide sequence of the Arabidopsis cDNA that complemented the PTR yeast deficiency was determined using the dideoxy chain-termination sequencing method of Sanger, F. et al. (*Proc. Natl. Acad. Sci. (U.S.A.)* 74:5463–5467 (1977)) using Sequenase Version ;2.0 (United States Biochemical, Cleveland, Ohio). A NotI, 2.8 kb cDNA fragment was cloned into Bluescript SKII (Stratagene, La Jolla, Calif.). An ExoIII/Mung Bean deletion kit (Stratagene, La Jolia, Calif.) was used to generate a deletion series of the fragment. Double-stranded template DNA was sequenced using $T_3$ and M13 primers of pBluescript. Standard molecular techniques, unless otherwise stated, were performed according to Sambrook, J. et al. (In: *Molecular Cloning A Laboratory Manual*, Cold Spring Harbor Laboratory, Cold Spring Harbor, N.Y. (1989)). Nucleotide and amino acid sequence analysis and comparisons were performed with the NCBI BLAST algorithm search program (Altschul, S. F. et al., *J. Molec. Biol.* 215:403–410 (1990)).

Figure 1C:
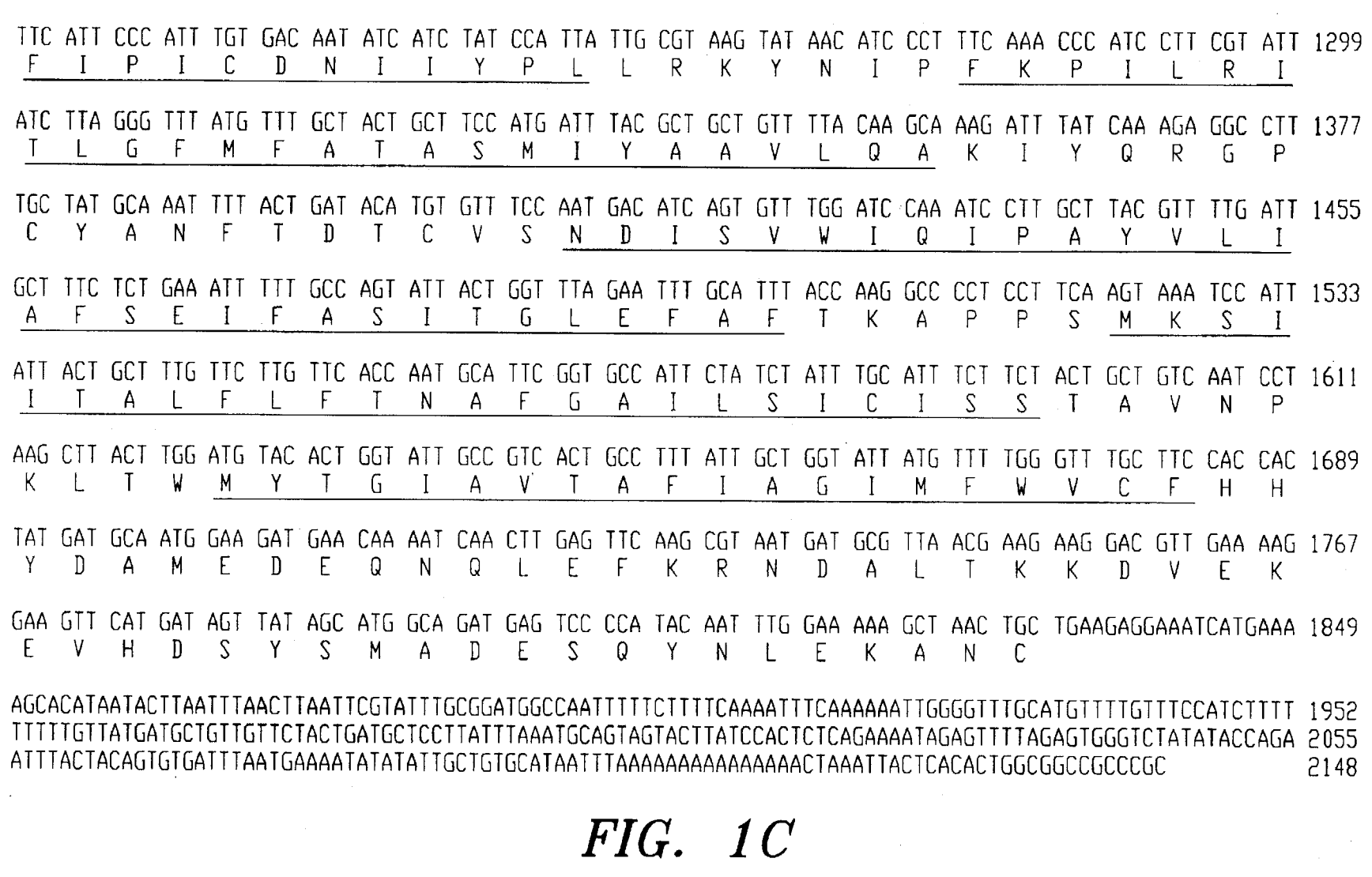

Such DNA sequence analysis of insert isolated from pPTF4 showed a 1833 bp open reading frame within the 2799 bp insert (FIG. 1 ). The open reading frame encoded a polypeptide of 610 amino acids (67,510 d). Hydropathy analysis (Kyte, J. et al., *J. Molec. Biol* 157:105–132 (1982)) showed the predicted protein, ATPTR2Ap, to be highly hydrophobic with 10–12 putative transmembrane domains. Four potential glycosylation sites were identified which favor a 12 transmembrane domain configuration. A search of the protein sequence data base using the NCBI BLAST algorithm (Altschul et al. 1990) revealed homologies to the yeast peptide transporter YSCPTR2p (probability High Score 654, 52% identity, 68% similarity) and to the *A. thaliana* nitrate transporter ATHCHL1p (Tsay, Y. F. et al., *Cell* 72:705–713 (1993)) (probability High Score 82, 36% identity, 47% similarity). FIG. 1 shows the nucleotide sequence of the atptr2a cDNA (SEQ ID NO:1) of plasmid pPTF4 and the deduced amino acid sequence of the encoded ATPTR2Ap protein (SEQ ID NO:2). FIG. 2 shows the nucleotide sequence of the atptr2b cDNA (SEQ ID NO:3) of plasmid pDTF1 and the deduced amino acid sequence of the encoded ATPTR2Bp protein (SEQ ID NO:4).

Protein sequences from ATPTR2A, SACPTR2, and ATHCHL1A were aligned with the program Pileup in the sequence analysis software package GCG (Devereux, J. et al., *Nuc. Acids Res.* 12:387–395 (1984); Genetics Computer Group 1991: The Program Manual for the GCG Sequence Analysis Software Package, Version 7, University Research Park, Madison, Wis. (1991)), and a consensus sequence was generated with the GCG program, Pretty, from the alignment generated with Pileup. Pileup aligns a group of related sequences using progressive pairwise alignments. The gap weight was 3.0 and the gap length weight was 0.10. A consensus sequence was generated by the GCG program, Pretty, using the output from Pileup. The consensus was generated at a minimum plurality of 2.00.

Protein sequences reported to be involved in peptide transport plus sequences from the ABC transporter superfamily were aligned again using the GCG Pileup program to produce a dendrogram displaying the sequence similarity relationships amongst all the proteins. The clustering strategy represented by the dendrogram is called UPGN1A (unweighted pair-group method using arithmetic averages which scores the similarity between every possible pair of sequences. The similarity scores are then used to create a clustering order that can be translated into a dendrogram where the horizontal branch lengths are proportional to the similarity between the sequences. The following data bases were used in the searches: GenBank, release 78.0; EMBL (Modified), release 35.0; Swiss-Prot, release 26.0

The sequence similarities divided into two groups. The first group (Group I) included proteins generally associated with ATP binding or those identified as having an ATP binding consensus sequence. The second group (Group II) included proteins containing hydrophobic segments and generally thought to be membrane bound. Within Group II, the ATPTR2A, SACPTR2, ATHCHL1A, and CaPTR (a *Candida albicans* peptide transporter) proteins comprised a smaller group distinct from any of the other groups in the analysis.

EXAMPLE 4

Peptide Transport Characteristics of the ATPTR2A and ATPTR2B Genes

The yeast peptide transport system has been shown to transport a wide variety of peptides with little discrimination between amino acid side-chains. To test whether this was the case for the plant transporter, a number of peptides varying in both composition and length were examined for their ability to support growth of pPTF4-transformed yeast.

Thus, the peptide transport mutant PB1X-9B and deletion strain PB1X-2AΔ transformed with plasmids pPTF4 (ATPTR2A) or pDTF1 (ATPTR2B) were grown on various peptides to assess the specificity of the plant peptide transporter. In addition, untransformed PB1X-9B, PB1X-9B transformed with plasmid pJP9 encoding the above-described yeast peptide transport gene, PB1X-2AΔ and PB1X-2A, the ptr2$^+$ parental strain to PB1X-2AΔ strain, were also assayed. Each strain was grown overnight in SC media plus uracil (non-transformed) or minus uracil (transformed) plus amino acids to stationary phase and harvested by centrifugation. Cells were then washed twice with sterile $dH_2O$ and resuspended at $5 \times 10^6$ cells/ml. 5 μl of each suspension was applied as a small spot to a 2 ml volume of solid media in a 24 well plate. All peptides were suspended in sterile, deionized water and added to an equal volume of SC medium plus the appropriate amino acids and uracil when required. The medium for each assay thus consisted of SC medium plus or minus uracil supplemented with 80 μM of a specific peptide and auxotrophic requirements minus the amino acid components of the added peptide. The plates were incubated at 30° C. for 72 hrs. and then scored for growth. Growth was scored as uniform colony formation compared to negative controls which showed no growth.

The mutant PBIX-9B was incapable of growing on any of the peptides. PBIX-9B transformed with pJP9 containing the yeast peptide transport gene showed growth on all peptides except tri-Lys, tetra-Lys (SEQ ID NO:5), poly-Lys, Met-Met-Leu and peptides longer than 3 amino acids (i.e. Gly-Leu-Gly-Leu (SEQ ID NO:6), Thr-Pro-Arg-Lys (SEQ ID NO:7), Tyr-Gly-Gly-Phe-Leu (SEQ ID NO:8), Trp-His-Trp-Leu-Gln-Leu (SEQ ID NO:9)). The plant peptide transport gene showed a similar pattern to that of yeast except that it was able to utilize Met-Met-Leu. The parent strain to the yeast peptide transport mutant PBIX-9B, PBIX-2A (his, leu, lys, ptr) also did not utilize Met-Met-Leu (data not shown). The results indicate that ATPTR2Ap transports both di- and tripeptides with a slightly different specificity than that of SACPTR2p (Table 1; N/A indicates not applicable due to the restoration of leucine prototrophy caused by the insertion of the leu2 gene in the host strain).

*Bacteriol.* 169:2132-2136 (1987)) Briefly, a filter disk containing 0.38 μmoles of the toxic compound was placed on a lawn containing 5×10⁶ cells and the plate incubated at 30° C for 1 to 2 days. Resulting halos were measured across their diameter. The toxic dipeptides Leu-Eth, Ala-Eth, Leu-F-Phe and Oxalysine were synthesized by standard solution phase techniques (Naider, F. et al., *J. Biol. Chem.* 249:9-20 (1974). The results of this experiment are shown in Table 2 (values are the mean of the diameters of the observed zone of inhibition in millimeters±standard error of the mean of at least two independent experiments).

TABLE 1

| Peptide | PBIX-9B | PBIX-9B (pJP9) | PBIX-9B (pPTF4) | PBIX-2AΔ (pDIF1) |
|---|---|---|---|---|
| Ala—Eth | R | S | S | R |
| Lys—Leu | − | + | + | N/A |
| His—Leu | − | + | + | N/A |
| His—Lys | − | + | + | + |
| Lys—Lys | − | + | + | + |
| tri-Lys | − | − | − | − |
| tetra-Lys | − | − | − | − |
| poly-Lys | − | − | − | − |
| Leu—Leu | − | + | + | N/A |
| tri-Leu | − | + | + | N/A |
| Ala—Leu | − | + | + | N/A |
| Ala—Ala—Leu | − | + | + | N/A |
| Ala—Lys | − | + | + | + |
| Lys—Ala—Ala | − | + | + | + |
| Met—Met—Leu | − | − | − | N/A |
| Gly—Leu—Gly—Leu | − | − | − | N/A |
| Thr—Pro—Arg—Lys | − | − | − | − |
| Tyr—Gly—Gly—Phe—Leu | − | − | − | N/A |
| Trp—His—Trp—Leu—Gln—Leu | − | − | − | − |
| SC—Ura | + | + | + | + |

EXAMPLE 5

Capacity of the ATPTR2A Gene to Alter Cellular Resistance or Sensitivity to Toxic Peptides As indicated above, peptides are frequently associated with plant diseases, exerting toxic or hormone-like effects on plant growth. Plants that are incapable of transporting such toxic peptides are resistant to such peptides. Such resistance can be obtained by mutating the ptr genes of the plant genome. Indeed, peptides containing a toxic amino acid analog have been used to characterize peptide transport (Island, M. D. et al., *J. Bacteriol.* 169:2132-2136 (1987)) and to isolate peptide transport genes (Island, M. D. et al., *Curr. Genet.* 20:457-463 (1991)).

Since ptr mutants are deficient in peptide transport, they are unable to take up toxic peptides. This inability renders such mutants resistant to the toxic effect of the peptides. In order to determine whether the polynucleotides of the present invention could restore toxic peptide sensitivity to ptr2 mutants, the sensitivity of plasmid-transformed cells was determined. Sensitivity to toxic amino acids and peptides was measured as described by Island, M. D. et al. (*J.*

TABLE 2

| | Strain | | | |
|---|---|---|---|---|
| Toxic Peptide | S288C | PB1X-9B | PB1X-9B (pJP9) | PB1X-9B (pPTF4) |
| Eth | 39.0 ± 3.0 | 44.5 ± 3.5 | 46.5 ± 1.5 | 46.5 ± 0.5 |
| F—Phe | 25.0 ± 4.0 | 14.0 ± 1.0 | 20.0 ± 0.0 | 19.5 ± 0.5 |
| Leu—Eth | 36.0 ± 2.0 | | 47.0 ± 1.0 | 45.0 ± 1.0 |
| Ala—Eth | 33.5 ± 2.5 | | 42.5 ± 2.5 | 35.0 ± 1.0 |
| Leu—F—Phe | 28.0 ± 4.0 | | 20.5 ± 3.0 | 37.0 ± 1.0 |
| Lys—Ala—Eth | 26.0 ± 3.0 | | 36.0 ± 1.5 | 37.5 ± 1.5 |
| Lys—Leu—Ala—Eth | 0 | 0 | 0 | 0 |
| Lys—Leu—Leu—Ala—Eth | 0 | 0 | 0 | 0 |
| Lys—Leu—Eth | 30.0 ± 0.0 | | 36.0 ± 0.5 | 35.0 ± 1.0 |
| Lys—Leu—Leu—Eth | 0 | 0 | 0 | 0 |
| Lys—Leu—Leu—Leu—Eth | 0 | 0 | 0 | 0 |

The peptide transport mutant PBIX-9B was found to be resistant to peptides containing the toxic amino acid analog ethionine. Transformation of PB1X-9B with the plasmid-borne yeast peptide transport gene restored sensitivity to these toxic compounds. PBIX-9B transformed with pPTF4 also restores sensitivity to the toxic dipeptides Ala-Eth, Leu-Eth and Leu-f-Phe (Table 2). The halos obtained on S288C and PB1X-9B (pJP9) with leu-F-Phe exhibited a hazy background within the halo; the halo obtained on PB1X-9B (pJP9) with Lys-Ala-Eth exhibited a broad border around within the halo.

The experiment thus demonstrates that whereas PBIX-9B showed complete resistance to the toxic peptides, both the mutant and transformant are sensitive to ethionine and fluorophenylalanine (F-Phe). In addition, the deletion strain PBIX-2AΔ also showed complete resistance to the toxic peptides. None of the strains tested were sensitive to Lys-Leu-Ala-Eth, Lys-Leu-Leu-Ala-Eth or to Lys-Leu-Leu-Eth, Lys-Leu-Leu-Leu-Eth. Both the yeast and plant peptide transporter showed similar patterns of sensitivity to toxic peptides with the plant peptide transporter expressed in yeast.

The yeast peptide transport mutant transformed with the Arabidopsis peptide transport gene thus showed similar sensitivity, as measured by halo size, and specificity to a range of toxic peptides as that of Saccharomyces wild type or peptide transport mutant transformed with the yeast peptide transport gene. Both transformants and wild type (S288C) are most sensitive to ethionine and ethionine containing peptides which produce the largest halos and appear less sensitive to fluorophenylalanine and Leu-f-Phe which is consistent with the data of Island, M. D. et al. (*J. Bacteriol.* 169:2132–2136 (1987)). S288C and the transformants are not sensitive to any of the toxic peptides with chain lengths four residues and longer. The data indicate this is most likely due to chain length as the tri-peptides Lys-Ala-Eth and Lys-Leu-Eth were toxic to both wild type and transformants while the longer peptides of similar composition were not toxic to the cells (Table 2). This is consistent with reports that wild type *Saccharomyces cerevisiae* does not readily transport peptides four residues and longer (Becker, J. M. et al., In: *Microorganisms and Nitrogen Sources*, Payne, J. W. (ed.), John Wiley and Sons, Inc., pp. 257–279 (1980)). However, this inability to take up longer peptides has not been tested with a wide range of peptides varying in amino acid side chain composition.

EXAMPLE 6

ATPTR2A-Mediated Uptake of Peptides in *S. cerevisiae*

The kinetics of ATPTR2A-mediated transport of peptides in yeast was evaluated by transforming pPTF4 into the *S. cerevisiae* peptide transport mutant, PBIX-9B and measuring the uptake of tritiated Leu-Leu dipeptide.

L-leucyl-L [$^3$H]leucine trifluoroacetic acid (TFA) was synthesized by standard solution phase techniques (Naider, F. et al., *J. Biol. Chem.* 249:9–20 (1974)). Uptake of L-leucyl-L-[H]leucine was performed as by Island, M. D. et al. (*J. Bacteriol.* 169:2132–2136 (1987)), with the following modifications. Cells were grown to late log phase (2–6×10$^7$ cells/ml) overnight in SC with 2% glucose, 1 mg/ml allantoin plus amino acids to supplement auxotrophic markers. To induce peptide transport, 5–15 ml from this culture was added to 100 ml fresh medium such that the density was 3.0×10$^6$ cells/ml. This culture was allowed to grow (approx. 2 hrs.) to a density of 6.0×10$^6$ cells/ml and then harvested by centrifugation. The pelleted cells were washed twice with 10 ml cold dH$_2$O and suspended in cold 2% glucose to a final concentration of 2×10$^8$ cells/ml and incubated at 30° C. for 15 min. 500 µl of cells were then added to an equal volume of reaction mixture (30° C.) and incubated at 30° C. At 20, 40, 60, 90, and 120 sec. intervals, 190 µl portions were removed, filtered over filters (pore size, 0.45 µm; GN-6; Gelman Sciences, Inc., Ann Arbor, Mich.) and washed 2 times with 5 ml cold, sterile dH$_2$O and once with 5 ml dH$_2$O at room temperatures. Filters were placed in scintillation vials with 5 ml of Budget-Solve scintillation cocktail (Research Products International Corp., Mount Prospect, Ill.) and counted (liquid scintillation counter; LS-7000; Beckman Instruments, Inc., Fullerton, Calif.). The final concentration of the components in the uptake assay was 1% glucose, 40 mM sodium citrate-potassium phosphate buffer (pH 5.5), and 1.5×10$^5$M L-leucyl-L-[$^3$H]leucine (specific activity, 10 mCi/mmole). Uptake is expressed as nanomoles per mg dry weight.

Transformation with pPTF4 restored [H$^3$]-dileucine uptake to wild-type levels (FIG. 3). Uptake of the radiolabeled substrate could be inhibited with 100-fold cold dileucine and 100-fold cold leucine had no effect on the uptake rate. Uptake rates conferred by the plant peptide transporter are also consistent with uptake rates of PBIX-9B transformed with the yeast peptide transporter. A number of peptides could compete for uptake of [H$^3$]-dileucine and uptake competition similar to that seen for Leu-Leu was also seen for Ala-Ala, Ala-Ala-Ala, Ala-M et, Met-Met-Leu, Met-Met and Leu-Phe in PBIX-9B transformed with pJP9 or pPTF4. γ-aminolevulinic acid, which is structurally similar to glycyl-glycine, and recently shown to be transported by the dpp operon in both *E. coil* and *Salmonella typhimurium* (Elliot, T. et al., *J. Bacteriol.* 175:325–331 (1993); Verkamp, E. et al, *J. Bacteriol.* 175:1452–1456 (1993)), did not compete with dileucine for uptake in PBIX-9B[pPTF4] while ALA was able to compete with radiolabeled dileucine uptake in PBIX-9B[pJP9], the yeast peptide transport system.

Yeast cells transformed with the plant peptide transport gene were thus able to take up radiolabeled dileucine to a level comparable to that of wild type. The fact that excess leucine did not reduce uptake indicated that the peptide is not transported via an amino acid transporter. Transport of dileucine was found to be inhibited by a number of peptides containing hydrophobic residues. This finding is consistent with the data from the peptide growth experiment and supports a strong bias toward transport of peptides composed in part or entirely of hydrophobic residues such as Ala-Ala, tri-Ala, Gly-Ile, Val-Val, Phe-Ala-Glu, Leu-Leu, Leu-Gly (Sopanen, T. et al., *FEBS Lett.* 79:4–7 (1977); Higgins, C. F. et al., *Planta* 138:211–216 (1978); Higgins, C. F. et al., *Planta* 142:299–305 (1978)). These studies also showed that Gly-Gly was a poor competitor for substrates such as Gly-Ile, tri-Ala and Ala-Ala which is supported by lack of inhibition of dileucine transport by ALA, a Gly-Gly analog, in yeast cells transformed with the plant peptide transport gene.

EXAMPLE 7

Sensitivity of *A. thaliana* to Toxic Peptides

To determine if the experimental results obtained with ATPTR2Ap expressed in yeast were comparable to ATPTR2Ap expressed in an Arabidopsis genetic background, toxic peptides were applied to Arabidopsis seedlings in an experiment analogous to the disk assay. Thus, *A. thaliana* seeds and seedlings were exposed to Ethionine, Ala-Eth, Leu-Eth, Leu-fluorophenylalanine or oxalysine containing peptides, and the minimum inhibitory concentrations (MIC) were determined for each of the toxic compounds.

Approximately 15 A. thaliana seeds were placed in a row at one end of 10 cm plate containing 20 ml of Arabidopsis growth media (Kranz and Kirchheim 1987). The seeds were incubated 3–5 days in the light with the plate set in an upright position. When the roots were approximately 1–2 cm long, sterile paper filter disks were placed immediately in front of the root tips on the right and left side of the plate 2 cm from the edge of the plate. A line was drawn across the plate using the top of the disks as a guide marking zero growth. 5 μl of toxic amino acid analog, toxic peptide, or toxic peptide plus competitor was added to one disk while $H_2O$ was place on the other disk. The plates were incubated for an additional 3–5 days. The average length of the roots was measured from the line and the results expressed as a percentage of control root growth.

To measure the minimum inhibitory concentration of the toxic peptides, 10 to 15 A. thaliana seeds were place on solid Arabidopsis growth media with decreasing concentrations of toxic peptide. The seeds were incubated for 4 days in the dark and then scored for germination.

Ala-Eth, Leu-Eth and Oxa-Lys were found to inhibit germination of A. thaliana seeds and root elongation of seedlings at 0.038 μmoles while ethionine inhibited germination and root elongation at 0.0038 μmoles. Both seed germination and root elongation was not inhibited by Leu-f-Phe. This inhibition did not appear to effect other parts of the plant as the leaves looked comparable to the unaffected control. Seeds exposed to ethionine, ethionine containing peptides as well as oxalysine (a toxic lysine analog) germinated and grew a root 1–2 mm in length after which growth was arrested suggesting that this peptide transport gene is not expressed immediately upon imbibation and germination but later, after the emergence of the root primordia.

Competitor peptides added with the toxic peptides showed differences in their ability to reverse toxicity of the ethionine containing peptides in the root assay. Ala-M et and Met-Met were able to reverse the toxicity of Ala-Eth which might be expected considering the similarity in structure. This was also the case for Leu-M et and Met-Met reversing the toxicity of Leu-Eth. Met, Ala-Ala, Ala-Ala-Ala, and ALA were unable to reverse the inhibition of root growth mediated by Ala-Eth or Leu-Eth (Table 3).

TABLE 3

| Competitor | Toxix Peptide | |
|---|---|---|
| | Ala—Eth | Leu—Eth |
| Met | 0 | 0 |
| Ala—Ala | 0 | 0 |
| tri-Ala | 0 | — |
| Met—Met | 40 | — |
| Ala—Met | 70 | — |
| Leu—Met | — | 100 |
| ALA | 0 | 0 |

A common feature between the yeast and plant peptide transporter is the lack of side-chain specificity of each of the peptide transport systems. In the results of the peptide growth assay, both systems are able to take up and utilize peptides which, in general, have a hydrophobic character to them. These peptides contain one or more of the hydrophobic amino acids alanine, leucine, or methionine. This was also generally the case with earlier work on S. cerevisiae and the barley system. Peptides containing two or more lysines did not support the growth of either the plant or yeast transformants. This finding is consistent with previous work which showed that peptides containing basic amino acids such as histidine or lysine or peptides with glycine as a component, did not support growth in yeast (Lichliter, W. D. et al., Agents Chemother 10:483–490 (1976); or plants (Sopanen, T. et al., Plant Physiol. 61:630:633 (1978); Higgins, C. F. et al., Planta 138:217–221 (1978); Higgins, C. F. et al., Planta 142:299–305 (1978)). The results from the toxic peptide disk assays also demonstrate little difference in specificity between the plant and yeast peptide transport systems (Table 2). One notable difference is the plant gene confers greater and more complete sensitivity, as judged by size and appearance of the halo, to leucine-fluorophenylalanine that does the yeast transport gene. Since very few phenylalanine containing peptides were tested, it is difficult to conclude whether this difference has any significance for the interaction of the peptide with its binding site between the two transporters.

EXAMPLE 8

ATPTR2A Expression in A. thaliana

The isolation of the ATPTR2A cDNA provided a probe capable of measuring the extent of ATPTR2A transcription in plant tissue.

The expression of atptr2a was determined by reverse transcription-polymerase chain reaction (RT-PCR). Reverse transcription and PCR were performed as described by Sambrook, J. et al. (In: Molecular Cloning A Laboratory Manual, Cold Spring Harbor Laboratory, Cold Spring Harbor, N.Y. (1989)).). Total RNA (10 μg), from roots and leaves of 7 day old Arabidopsis seedlings grown on defined media under sterile conditions, was pretreated with RNase-free DNase and reverse transcribed with AMV reverse transcriptase using an oligo dT primer. The first-strand synthesized cDNA (treated with RNase A) was amplified by PCR (94° C., 1 min.; 55° C., 1.5 min.; 72° C., 1.5 min.; 30 cycles) by Taq polymerase (Promega Corp. Madison, Wis.). The primers used were an upstream primer starting at base 1975 (SEQ ID NO:10):

SEQ ID NO:10 GCTTCCATGATTTACGCTGC and a downstream primer starting at base 2528 (SEQ ID NO:11):

SEQ ID NO:11 GCATAAACGCCTACCGG

The primers generate a 569 bp fragment of the open reading frame of atptr2a. The amplified DNAs were electrophoresed and transferred to nitrocellulose filters. The filters were probed with an α-$^{32}$P-dCTP labeled 720 bp BamHI-NotI DNA fragment from plasmid pFL61 containing the atptr2a gene. The blots were exposed to autoradiographic film at −80° C. for 24 hrs. The blots revealed that atptr2a expression occurs in the roots of in vitro grown Arabidopsis seedlings. The probe also hybridized to total RNA from seedling leaves, and PCR generated products from plasmid pFL61 harboring the atptr2a gene and Arabidopsis genomic DNA.

The results indicate that Arabidopsis seedlings germinated under defined growth conditions expressed the ATPTR2A peptide transporter in the roots and the leaves.

This data supports the results of the root assay indicating that Arabidopsis seedlings express a root specific peptide transporter which can transport toxic and non-toxic peptides.

Transport has been reported in root tips and aleurone layers of germinated barley grains but at uptake levels less than 1% of that seen with scutella (Sopanen, T. et al., *Plant Physiol.* 61:630:633 (1978)). Results from the seed and seedling experiments, in which Arabidopsis seeds exposed to toxic peptides were able to germinate and inhibition of root growth by toxic peptides occurred with roots 1–2 cm in length, indicated that the expression of the peptide transporter reported here is root and not seed specific which would imply a transport system different from that described for barley grains. However, this difference may be more related to expression of the target of the toxic amino acid analog rather than the ability to transport the peptide. Indeed, Payne, J. W. et al. (*Planta* 170:263–271 (1987)) identified two proteins which were shown to be involved with peptide transport in barley grains, one of which was approximately 65–67 kd in size which is in good agreement with the 67.5 kd size predicted for ATPTR2Ap. These proteins become detectable in a scutellar epithelia extract after 15 hrs. imbition, coincident with an increase in peptide transport activity, and remain present three days after the onset of germination. This lag in protein expression is similar to the lag in toxicity seen in germinating Arabidopsis seeds which may indicate that the peptide transport system identified here is similar or identical to the one described for barley grains.

Clearly, from a physiological standpoint, the Arabidopsis peptide transporter exhibits transport characteristics similar to that of the yeast peptide transporter including transport of peptides with similar chain length and composition as well as inhibition of transport by various competing peptide substrates. Sequence comparison between these two proteins also shows considerable similarity at the sequence level. Adding the ATHCHL1A sequence to the comparison produces a consensus sequence which shows homology generally confined to the hydrophobic segments of each of the polypeptides. This result, however, may have more to do with these proteins presumably being membrane bound rather than their function as transporters. When these same proteins, including the CaPTR protein, are compared to other transport proteins, they clearly comprise a distinct, separate group, designated Group III. Since other proteins in this comparison also contain hydrophobic segments, such as the Tap and Mdl proteins and the b and c components of the bacterial transporters, and they are not grouped along with Group III proteins, the resulting clustering order indicates conserved consensus sequences among particular groups of proteins which are conserved for other reasons than their association with a particular subcellualr structure. Interestingly, the most closely related group to Group III is composed of two clusters of proteins (Group IV and Group V) reported to be the membrane bound components of bacterial peptide transporters (Perego, M. et al., *Mol. Microbiol.* 5:173–185 (1991); Rudner, D. Z. et al., *J. Bacteriol.* 173:1388–1398 (1991); Mathiopoulos, C. et al., *Mol. Microbiol.* 5:1903–1913 (1991); Hiles, I. D. et al., *J. Molec. Biol* 195:125–142 (1987); Alloing, G. et al., *Mol. Microbiol.* 4:633–644 1990)). These proteins are postulated to mediate the passage of peptides across the plasma membrane (Pearce, S. R. et. al, *Mol. Microbiol.* 6:47–57 (1992)). So, while these three groups of proteins have similar topology and function, their sequence conservation suggests they evolved into separate families of proteins.

Other functions of plant peptide transport other than a nutritional one postulated for barley grains are not known, though a wide range of peptides and peptide compounds are known to occur in plants (Higgins, C. F. et al., In: *Encyclopedia of Plant Phsyiology, N.S.*, volume 14A, Boulter, D. et al. (eds.) Springer, N.Y., pp. 438–458 (1982)). Clearly, more research in this area is necessary. Isolation of a plant peptide transport gene does bring about the possibility of exploiting this system for delivery of toxic or growth promoting substances to plants in a manner analogous to that postulated for human pathogens (Fickel, T. E. et al., *Nature New Biol* 241:161–163 (1973); Higgins, C. F. et al., *Nature* 327:655–656 (1987)).

Thus, the above-described yeast mutants were used to clone an *Arabidopsis thaliana* peptide transport gene that was capable of functionally complementing the yeast peptide transport mutant. The plant peptide transporter (ATPTR2Ap) conferred growth on di- and tripeptides but not peptides four residues and higher. The plant peptide transporter also conferred sensitivity to a variety of ethionine-containing, toxic peptides of chain length three or less, and the ability to take up radiolabeled dileucine at levels similar to wild type. Dileucine uptake was reduced by the addition of a variety of growth-promoting peptides. Root growth of *A. thaliana* seedlings exposed to ethionine-containing, toxic peptides was inhibited and growth could be restored by addition of various peptides shown to compete with dileucine uptake in yeast expressing the *A. thaliana* transport gene. The peptide transporter is expressed in the roots and leaves of *A. thaliana* seedlings. The sequence of a cDNA insert of 2.8 kb indicated an open reading frame encoding a 610 amino acid polypeptide (67.5 kd). Hydropathy analysis predicted a highly hydrophobic protein with 12 potential hydrophobic segments. The plant peptide transporter shows homology to ATHCHL1A, the nitrate inducible nitrate transporter and considerable homology to the *S. cerevisiae* peptide transporter SACPTR2, but little homology to other proteins known to be involved in peptide transport. This represents the first reported sequence of a plant peptide transporter and the third protein identified in a potentially new family of membrane transport proteins.

The recognition that the yeast and plant peptide transport systems share a number of characteristics supports the idea that structural components of these systems may be homologous. In separate studies with *Saccharomyces cerevisiae* and barley grains, competition experiments demonstrated complete inhibition of dipeptide uptake by tripeptides, and vice versa, indicating that the same peptide transport system transports both di- and tri-peptides (Sopanen, T. et al., *FEBS Lett.* 79:4–7 (1977); Higgins, C. F. et al., *Planta* 138:217–221 (1978); Marder, R. et al., *J. Bactiol.* 131:906–916 (1977); Becker, J. M. et al., *Arch. Biochem. Biophys.* 178:245–255 (1977)).

Transport of peptides containing D-residues is reduced in both plants and yeast although this is somewhat position dependent. D-residues at the C-terminal end of the peptide are not transported in plants while peptides with D-residues at the N-terminus are taken up but at a reduced rate (Higgins, C. F. et al., *Planta* 142:299–305 (1978); Higgins, C. F. et al., *Planta* 138:211–216 (1978)). Similar results have been obtained in yeast in that although peptides with a D-residue at the C-terminus are transported, such transport is at a lower rate than those with D-residues at the N-terminus (Becker, J. M. et al., In: *Microorganisms and Nitrogen Sources*, Payne, J. W. (ed.), John Wiley and Sons, Inc., pp. 257–279 (1980)).

A number of similarities are present concerning the energetics of both peptide transport systems. Both have an acidic pH optima for transport (pH 5.5 for yeast, pH 3.8 for barley seeds) and both exhibit saturation kinetics (Higgins, C. F. et al., *Planta* 138:217–221 (1978); Becker, J. M. et al., *Arch. Biochem. Biophys.* 178:245–255 (1977)). Energy uncouplers such as sodium azide, dinitrophenol, and potassium cyanide all cause complete inhibition of transport of peptides in both yeast and plants (Higgins, C. F. et al., *Planta* 138:217–221 (1978); Becker, J. M. et al., *Arch. Biochem. Biophys.* 178:245–255 (1977)).

In sum, the above-described experiments demonstrate the ability of an *A. thaliana* gene to restore peptide transport to a *S. cerevisiae* mutant unable to transport di- and tripeptides. The yeast mutant transformed with the *A. thaliana* gene conferred sensitivity to toxic peptides, allowed growth of the mutant on a wide variety of peptides, and restored uptake of radiolabled dileucine. Growth of *A. thaliana* roots was inhibited by toxic peptides and this inhibition was reversed by a number of peptide competitors which is consistent with the peptide transporters' expression in the roots. This plant peptide transport gene encodes a protein which shows a high degree of homology to the Arabidopsis nitrate transporter ATHCHL1Ap and to the yeast peptide transporter SACPTR2p and is the third in a growing group of proteins whose derived consensus sequence shows little homology to other proteins involved in peptide transport.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A substantially purified polynucleotide which encodes a plant peptide transport protein, has a length greater than 10 nucleotide residues, and hybridizes under low stringency conditions to a nucleotide of SEQ ID NO:1 or SEQ ID NO:3.

2. The polynucleotide of claim 1 which encodes a functional transport protein.

3. The polynucleotide of claim 1 which encodes a non-functional plant transport protein, wherein the presence of said polynucleotide impairs a capacity of a plant cell to transport peptides.

4. The polynucleotide of claim 1 which encodes a non-functional fragment of a functional plant peptide transport protein.

5. The polynucleotide of claim 1 which encodes a peptide transport protein of *Arabidopsis thaliana*.

6. The peptide transport protein of claim 5 which is ATPTR2Ap.

7. The peptide transport protein of claim 5 which is ATPTR2Bp.

8. A vector which comprises the polynucleotide of claim 1.

9. The vector of claim 8 which is a Ti plasmid.

10. The vector of claim 8 which is a CaMV vector.

11. A transformed plant cell which contains a substantially purified polynucleotide which encodes a plant peptide transport protein, which polynucleotide has a length greater than 10 nucleotide residues, and hybridizes under low stringency conditions to a nucleotide of SEQ ID NO:1 or SEQ ID NO:3.

12. The plant cell of claim 11 wherein said polynucleotide encodes a functional transport protein.

13. The plant cell of claim 11, wherein said polynucleotide encodes a non-functional transport protein or a non-functional fragment of a peptide transport protein, and wherein the presence of said polynucleotide impairs a capacity of said cell to transport peptides.

14. A transformed plant containing the plant cell of claim 12.

15. A transformed plant containing the plant cell of claim 13.

16. A method for increasing the resistance of a plant to an herbicidal peptide which comprises providing a polynucleotide to cells of said plant, said polynucleotide hybridizing under low stringency conditions to a nucleotide of SEQ ID NO: 1 or SEQ ID NO: 3 and encoding a mutated plant peptide transport protein or a fragment of a plant peptide transport protein, wherein the presence of said polynucleotide and its recombination with the cells' endogenous peptide transport gene impairs the capacity of said cells to transport a plant herbicidal peptide, and thereby increases the resistance of said plant to said herbicidal peptide.

17. The method of claim 16, wherein said polynucleotide encodes a mutated peptide transport protein of *Arabidopsis thaliana*.

18. The method of claim 17, wherein said mutated peptide transport protein is a mutated ATPTR2Ap peptide transport protein of *Arabidopsis thaliana*.

19. The method of claim 17, wherein said mutated peptide transport protein is a mutated ATPTR2Bp peptide transport protein of *Arabidopsis thaliana*.

20. The method of claim 16, wherein said herbicidal peptide is produced by a fungal pathogen.

21. The polynucleotide of claim 1 which is an antisense oligonucleotide which is capable of hybridizing to a target mRNA molecule or its corresponding endogenous peptide transport gene, and thereby impairs the translation of the mRNA molecule into the gene product or the transcription of the gene into the corresponding mRNA, respectively.

22. The plant of claim 11 wherein the polynucleotide is an antisense oligonucleotide which is capable of hybridizing to a target mRNA molecule or its corresponding endogenous peptide transport gene, and thereby impairs the translation of the mRNA molecule into the gene product or the transcription of the gene into the corresponding mRNA, respectively.

23. The polynucleotide of claim 1 which is gene atptr2a which has the cDNA sequence shown by SEQ ID NO:1.

24. The polynucleotide of claim 1 which is gene atptr2b which has the cDNA sequence shown by SEQ ID NO:3.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 2799 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Arabidopsis thalliana ( v i i ) IMMEDIATE SOURCE:
( B ) CLONE: atptr2a ( x i ) SEQUENCE DESCRIPTION: SEQ ID NO:1:

```
GCGGCCGCCA GTGTGAGTAA TTTAGGAGAA ATTCAAAAAC CTTGAGTGGA AACTCCTCAT      60

CGTTCGTATA ATAATCGTTT GACCTCTTTT GTTGGAGTT GGGACTTTCT CCACACTTTC      120

ACATACATAC ACTTTTAATT TCCAAGTATT TATTTAATAC ATTAAGGAAA AATTTTTTCA     180

TTCTAAAAAT TTTTCTTTTT TTATTATTAT TGTCATAAAT ACTTATTTGT TGTTGTGTAT     240

ATTTAATCTT GTTTTAAATA CCCTTTCTCA CTCTCACTCA CTTTCATATT TCTTACTCTT     300

AGTTGAGTTA GTCGGCCTTC GATACACATA TAAAAGTGTT TATTTAACT TTTTTGTGAA      360

TTCACTTGTC AATTTTGTGT AATTAGTTTG ACTAATTATT ATTATTATTA TTTTTGATCT     420

ATTCTTTTTT TTATCTTTTG TACTACATTG TTTTTTAATC TTTCGCTTGT TTACGTTATT     480

TTTCTCTTCC TCTTTTTTCC CTTTTAATAT TCGCCTCTTT TGTTTTCTCG TTTCATTGTA     540

ATTATTTTAT ACCCAAAAAT TGTTCTTGAA ACTTCTGTTC ATTCTCTTTT TTATTATTAT     600

TTTTGATTTT CATACGATCG ATTTCCTACA TTCAATTTAC CTGTGTTTAC AATGAGTAGC     660

ATTGAAGAAC AAATTACGAA ATCGGACTCC GATTTCATCA TTTCAGAAGA TCAATCCTAC     720

TTAAGCAAGG AGAAAAAGGC TGATGGTTCT GCCACCATCA ACCAAGCTGA CGAACAATCC     780

TCCACCGATG AACTCCAAAA ATCCATGTCC ACCGGCGTCC TCGTCAATGG TGACTTATAC     840
```

| | | | | | | |
|---|---|---|---|---|---|---|
| CCTTCTCCTA | CCGAAGAAGA | ATTAGCCACC | CTTCCTAGTG | TTTGCGGTAC | TATTCCTTGG | 900 |
| AAAGCCTTTA | TTATCATTAT | TGTCGAGCTT | TGCGAACGTT | TCGCTTACTA | TGGACTCACT | 960 |
| GTTCCCTTTC | AAAATTATAT | GCAATTCGGT | CCTAAGGATG | CTACTCCAGG | TGCCCTTAAT | 1020 |
| TTAGGCGAAA | CCGGTGCTGA | CGGTCTTTCT | AATTTCTTCA | CATTTTGGTG | TTATGTCACC | 1080 |
| CCGGTTGGCG | CTGCACTTAT | TGCTGATCAA | TTCCTTGGTA | GGTACAATAC | CATTGTTTGC | 1140 |
| TCTGCTGTCA | TTTACTTTAT | TGGTATCTTG | ATTCTTACAT | GTACTGCTAT | TCCTTCTGTC | 1200 |
| ATTGATGCCG | GAAAAGTAT | GGGTGGGTTT | GTCGTCTCTT | TGATCATCAT | TGGGCTTGGA | 1260 |
| ACCGGTGGTA | TCAAATCCAA | TGTTTCCCCC | TTGATGGCTG | AACAGCTTCC | AAAAATTCCT | 1320 |
| CCTTATGTAA | AGACAAAGAA | AAATGGTAGC | AAGGTCATTG | TTGACCCAGT | CGTCACCACC | 1380 |
| TCTCGTGCCT | ATATGATTTT | CTACTGGACA | ATTAACGTCG | GTTCTCTCTC | CGTATTAGCC | 1440 |
| ACAACTAGTT | TGGAAAGTAC | TAAAGGTTTT | GTTACGCAT | ACTTGCTTCC | CTTGTGCGTC | 1500 |
| TTTGTTATCC | CCTTAATTAT | TTTGGCTGTT | AGTAAGACAG | CTTTTACAAG | CACACTCCTC | 1560 |
| CCTCCGGTTC | CATCTTTGTT | CGTGTTGGTC | AAGTGTTCTT | CCTTGCTGCT | CAAAACAAAT | 1620 |
| TTAATCTCGA | AAAAACTAAA | CCATCTTGCA | CTACTACTGT | TGGAGCGTTA | CGTCAAGGAT | 1680 |
| CAGTGGGATG | ACTTGTTTAT | CGACGAATTG | AAACGTGCCT | TACGCGCCTG | CAAAACTTTT | 1740 |
| CTCTTTTACC | CTATCTATTG | GGTATGCTAT | GGTCAAATGA | CCAACAACTT | AATTTCTCAA | 1800 |
| GCTGGACAAA | TGCAAACGGG | TAATGTCTCT | AACGATCTTT | TCCAAGCCTT | CGATTCAATC | 1860 |
| GCCTTGATTA | TTTTCATTCC | CATTTGTGAC | AATATCATCT | ATCCATTATT | GCGTAAGTAT | 1920 |
| AACATCCCTT | TCAAACCCAT | CCTTCGTATT | ACTTTAGGGT | TTATGTTTGC | TACTGCTTCC | 1980 |
| ATGATTTACG | CTGCTGTTTT | ACAAGCAAAG | ATTTATCAAA | GAGGCCCTTG | CTATGCAAAT | 2040 |
| TTTACTGATA | CATGTGTTTC | CAATGACATC | AGTGTTTGGA | TCCAAATCCC | TGCTTACGTT | 2100 |
| TTGATTGCTT | TCTCTGAAAT | TTTTGCCAGT | ATTACTGGTT | TAGAATTTGC | ATTACCAAG | 2160 |
| GCCCCTCCTT | CAATGAAATC | CATTATTACT | GCTTTGTTCT | TGTTCACCAA | TGCATTCGGT | 2220 |
| GCCATTCTAT | CTATTTGCAT | TTCTTCTACT | GCTGTCAATC | CTAAGCTTAC | TTGGATGTAC | 2280 |
| ACTGGTATTG | CCGTCACTGC | CTTTATTGCT | GGTATTATGT | TTTGGGTTTG | CTTCCACCAC | 2340 |
| TATGATGCAA | TGGAAGATGA | ACAAAATCAA | CTTGAGTTCA | AGCGTAATGA | TGCGTTAACG | 2400 |
| AAGAAGGACG | TTGAAAAGGA | AGTTCATGAT | AGTTATAGCA | TGGCAGATGA | GTCCCAATAC | 2460 |
| AATTTGGAAA | AAGCTAACTG | CTGAAGAGGA | AATCATGAAA | AGCACATAAT | ACTTAATTTA | 2520 |
| ACTTAATTCG | TATTTGCGGA | TGGCCAATTT | TTCTTTTCAA | AATTTCAAAA | AATTGGGGTT | 2580 |
| TGCATGTTTT | GTTTCCATCT | TTTTTTTTGT | TATGATGCTG | TTGTTCTACT | GATGCTCCTT | 2640 |
| ATTTAAATGC | AGTAGTACTT | ATCCACTCTC | AGAAAATAGA | GTTTACAGT | GGGTCTATAT | 2700 |
| ACCAGAATTT | ACTACAGTGT | GATTTAATGA | AAATATATAT | TGCTGTGCAT | AATTTAAAAA | 2760 |
| AAAAAAAAAA | CTAAATTACT | CACACTGGCG | GCCGCCCGC | | | 2799 |

( 2 ) INFORMATION FOR SEQ ID NO:2:

( i ) SEQUENCE CHARACTERISTICS:
        ( A ) LENGTH: 610 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Arabidopsis thalliana ( v i i ) IMMEDIATE SOURCE:
    ( B ) CLONE: ATPTR2Ap ( x i ) SEQUENCE DESCRIPTION: SEQ ID NO:2:

```
Met Ser Ser Ile Glu Glu Gln Ile Thr Lys Ser Asp Ser Asp Phe Ile
 1           5                   10                  15

Ile Ser Glu Asp Gln Ser Tyr Leu Ser Lys Glu Lys Lys Ala Asp Gly
            20                  25                  30

Ser Ala Thr Ile Asn Gln Ala Asp Glu Gln Ser Ser Thr Asp Glu Leu
        35                  40                  45

Gln Lys Ser Met Ser Thr Gly Val Leu Val Asn Gly Asp Leu Tyr Pro
    50                  55                  60

Ser Pro Thr Glu Glu Glu Leu Ala Thr Leu Pro Ser Val Cys Gly Thr
65                  70                  75                  80

Ile Pro Trp Lys Ala Phe Ile Ile Ile Val Glu Leu Cys Glu Arg
                85                  90                  95

Phe Ala Tyr Tyr Gly Leu Thr Val Pro Phe Gln Asn Tyr Met Gln Phe
                100                 105                 110

Gly Pro Lys Asp Ala Thr Pro Gly Ala Leu Asn Leu Gly Glu Thr Gly
                115                 120                 125

Ala Asp Gly Leu Ser Asn Phe Phe Thr Phe Trp Cys Tyr Val Thr Pro
130                 135                 140

Val Gly Ala Ala Leu Ile Ala Asp Gln Phe Leu Gly Arg Tyr Asn Thr
145                 150                 155                 160

Ile Val Cys Ser Ala Val Ile Tyr Phe Ile Gly Ile Leu Ile Leu Thr
                165                 170                 175

Cys Thr Ala Ile Pro Ser Val Ile Asp Ala Gly Lys Ser Met Gly Gly
                180                 185                 190

Phe Val Val Ser Leu Ile Ile Ile Gly Leu Gly Thr Gly Gly Ile Lys
            195                 200                 205

Ser Asn Val Ser Pro Leu Met Ala Glu Gln Leu Pro Lys Ile Pro Pro
210                 215                 220

Tyr Val Lys Thr Lys Lys Asn Gly Ser Lys Val Ile Val Asp Pro Val
225                 230                 235                 240

Val Thr Thr Ser Arg Ala Tyr Met Ile Phe Tyr Trp Thr Ile Asn Val
                245                 250                 255

Gly Ser Leu Ser Val Leu Ala Thr Thr Ser Leu Glu Ser Thr Lys Gly
                260                 265                 270

Phe Val Tyr Ala Tyr Leu Leu Pro Leu Cys Val Phe Val Ile Pro Leu
            275                 280                 285

Ile Ile Leu Ala Val Ser Lys Thr Ala Phe Thr Ser Thr Leu Leu Pro
    290                 295                 300

Pro Val Pro Ser Leu Phe Val Leu Val Lys Cys Ser Ser Leu Leu Leu
305                 310                 315                 320

Lys Thr Asn Leu Ile Ser Lys Lys Leu Asn His Leu Ala Leu Leu Leu
                325                 330                 335

Leu Glu Arg Tyr Val Lys Asp Gln Trp Asp Asp Leu Phe Ile Asp Glu
            340                 345                 350

Leu Lys Arg Ala Leu Arg Ala Cys Lys Thr Phe Leu Phe Tyr Pro Ile
            355                 360                 365

Tyr Trp Val Cys Tyr Gly Gln Met Thr Asn Asn Lys Ile Ser Gln Ala
370                 375                 380

Gly Gln Met Gln Thr Gly Asn Val Ser Asn Asp Leu Phe Gln Ala Phe
385                 390                 395                 400
```

| | | | | | | | | | | | | | | |
|---|---|---|---|---|---|---|---|---|---|---|---|---|---|---|
|Asp|Ser|Ile|Ala|Leu 405|Ile|Ile|Phe|Ile|Pro 410|Ile|Cys|Asp|Asn|Ile Ile 415|
|Tyr|Pro|Leu|Leu 420|Arg|Lys|Tyr|Asn|Ile 425|Pro|Phe|Lys|Pro|Ile 430|Leu Arg|
|Ile|Thr|Leu 435|Gly|Phe|Met|Phe|Ala 440|Thr|Ala|Ser|Met|Ile 445|Tyr|Ala Ala|
|Val|Leu 450|Gln|Ala|Lys|Ile|Tyr 455|Gln|Arg|Gly|Pro|Cys 460|Tyr|Ala|Asn Phe|
|Thr 465|Asp|Thr|Cys|Val|Ser 470|Asn|Asp|Ile|Ser|Val 475|Trp|Ile|Gln|Ile Pro 480|
|Ala|Tyr|Val|Leu|Ile 485|Ala|Phe|Ser|Glu|Ile 490|Phe|Ala|Ser|Ile|Thr Gly 495|
|Leu|Glu|Phe|Ala 500|Phe|Thr|Lys|Ala|Pro 505|Pro|Ser|Met|Lys|Ser 510|Ile Ile|
|Thr|Ala|Leu 515|Phe|Leu|Phe|Thr|Asn 520|Ala|Phe|Gly|Ala|Ile 525|Leu|Ser Ile|
|Cys|Ile 530|Ser|Ser|Thr|Ala|Val 535|Asn|Pro|Lys|Leu|Thr 540|Trp|Met|Tyr Thr|
|Gly 545|Ile|Ala|Val|Thr|Ala 550|Phe|Ile|Ala|Gly|Ile 555|Met|Phe|Trp|Val Cys 560|
|Phe|His|His|Tyr|Asp 565|Ala|Met|Glu|Asp|Glu 570|Gln|Asn|Gln|Leu|Glu Phe 575|
|Lys|Arg|Asn|Asp 580|Ala|Leu|Thr|Lys|Lys 585|Asp|Val|Glu|Lys|Glu 590|Val His|
|Asp|Ser|Tyr 595|Ser|Met|Ala|Asp|Glu 600|Ser|Gln|Tyr|Asn|Leu 605|Glu|Lys Ala|
|Asn|Cys 610| | | | | | | | | | | | | |

( 2 ) INFORMATION FOR SEQ ID NO:3:

( i ) SEQUENCE CHARACTERISTICS:
        ( A ) LENGTH: 1939 base pairs
        ( B ) TYPE: nucleic acid
        ( C ) STRANDEDNESS: double
        ( D ) TOPOLOGY: linear ( i i ) MOLECULE TYPE: cDNA ( i v ) ANTI-SENSE: NO ( v i ) ORIGINAL SOURCE:
        ( A ) ORGANISM: Arabidopsis Thalliana
        ( B ) STRAIN: atptr2b ( x i ) SEQUENCE DESCRIPTION: SEQ ID NO:3:

```
GCGGCCGCCA GTGTGAGTAA TTTAGCGAAA ACGATGGGTT CCATCGAAGA AGAAGCAAGA      60
CCTCTCATCG AAGAAGGTTT AATTTTACAG GAAGTGAAAT TGTATGCTGA AGATGGTTCA     120
GTGGACTTTA ATGGAAACCC ACCATTGAAG GAGAAAACAG GAAACTGGAA AGCTTGTCCT     180
TTTATTCTTG GTAATGAATG TTGTGAGAGG CTAGCTTACT ATGGTATTGC TGGGAATTTA     240
ATCACTTACC TCACCACTAA GCTTCACCAA GGAAATGTTT CTGCTGCTAC AAACGTTACC     300
ACATGGCAAG GGACTTGTTA TCTCACTCCT CTCATTGGAG CTGTTCTGGC TGATGCTTAC     360
TGGGACGTT ACTGGACCAT CGCTTGTTTC TCCGGGATTT ATTTCATCGG GATGTCTGCG     420
TTAACTCTTT CAGCTTCAGT TCCGGCATTG AAGCCAGCGG AATGTATTGG TGACTTTTGT     480
CCATCTGCAA CGCCAGCTCA GTATGCGATG TTCTTTGGTG GGCTTTACCT GATCGCTCTT     540
```

-continued

```
GGAACTGGAG GTATCAAACC GTGTGTCTCA TCCTTCGGTG CCGATCAGTT TGATGACACG      600
GACTCTCGGG AACGAGTTAG AAAAGCTTCG TTCTTTAACT GGTTTTACTT CTCCATCAAT      660
ATTGGAGCAC TTGTGTCATC TAGTCTTCTA GTTTGGATTC AAGAGAATCG GGGTGGGGT       720
TTAGGGTTTG GGATACCAAC AGTGTTCATG GGACTAGCCA TTGCAAGTTT CTTCTTTGGC      780
ACACCTCTTT ATAGGTTTCA GAAACCTGGA GGAAGCCCTA TAACTCGGAT TTCCCAAGTC      840
GTGGTTGCTT CGTTCCGGAA ATCGTCTGTC AAAGTCCCTG AAGACGCCAC ACTTCTGTAT      900
GAAACTCAAG ACAAGAACTC TGCTATTGCT GGAAGTAGAA AAATCGAGCA TACCGATGAT      960
TGCCAGTATC TTGACAAAGC CGCTGTTATC TCAGAAGAAG AATCGAAATC CGGAGATTAT     1020
TCCAACTCGT GGAGACTATG CACGGTTACG CAAGTCGAAG AACTCAAGAT TCTGATCCGA     1080
ATGTTCCCAA TCTGGGCTTC TGGTATCATT TTCTCAGCTG TATACGCACA AATGTCCACA     1140
ATGTTTGTTC AACAAGGCCG AGCCATGAAC TGCAAAATTG GATCATTCCA GCTTCCTCCT     1200
GCAGCACTCG GGACATTCGA CACAGCAAGC GTCATCATCT GGGTGCCGCT CTACGACCGG     1260
TTCATCGTTC CCTTAGCAAG AAAGTTCACA GGAGTAGACA AAGGATTCAC TGAGATACAA     1320
AGAATGGGAA TTGGTCTGTT TGTCTCTGTT CTCTGTATGG CAGCTGCAGC TATCGTCGAA     1380
ATCATCCGTC TCCATATGGC CAACGATCTT GGATTAGTCG AGTCAGGAGC CCCAGTTCCC     1440
ATATCCGTCT TGTGGCAGAT TCCACAGTAC TTCATTCTCG GTGCAGCCGA AGTATTCTAC     1500
TTCATCGGTC AGCTCGAGTT CTTCTACGAC CAATCTCCAG ATGCAATGAG AAGCTTGTGC     1560
AGTGCCTTAG CTCTTTTGAC CAATGCACTT GGTAACTACT TGAGCTCGTT GATCCTCACG     1620
CTCGTGACTT ATTTTACAAC AAGAAATGGG CAAGAAGGTT GGATTTCGGA TAATCTCAAT     1680
TCAGGTCATC TCGATTACTT CTTCTGGCTC TTGGCTGGTC TTAGCCTTGT GAACATGGCG     1740
GTTTACTTCT TCTCTGCTGC TAGGTATAAG CAAAAGAAAG CTTCGTCGTA GTAATGCTGT     1800
TATCTATCTA CTTTCATTAC ATACAAAAGT TTGTTTCTTT CAACTGTAAC TGTCTCTGTA     1860
TCAATAACAA CATTGCTGTG TACTTTTCCT TTCAATTTCA AAAGTTTAAG TCGCCTAAAT     1920
TACTCACACT GGCGGCCGC                                                  1939
```

( 2 ) INFORMATION FOR SEQ ID NO:4:

( i ) SEQUENCE CHARACTERISTICS:
        ( A ) LENGTH: 585 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Arabidopsis thalliana ( v i i ) IMMEDIATE SOURCE:
        ( B ) CLONE: AtPTR2Bp ( x i ) SEQUENCE DESCRIPTION: SEQ ID NO:4:

```
Met Gly Ser Ile Glu Glu Glu Ala Arg Pro Leu Ile Glu Glu Gly Leu
 1               5                  10                  15

Ile Leu Gln Glu Val Lys Leu Tyr Ala Glu Asp Gly Ser Val Asp Phe
                20                  25                  30

Asn Gly Asn Pro Pro Leu Lys Glu Lys Thr Gly Asn Trp Lys Ala Cys
            35                  40                  45

Pro Phe Ile Leu Gly Asn Glu Cys Cys Glu Arg Leu Ala Tyr Tyr Gly
        50                  55                  60
```

```
Ile Ala Gly Asn Leu Ile Thr Tyr Leu Thr Thr Lys Leu His Gln Gly
65                  70                  75                  80

Asn Val Ser Ala Ala Thr Asn Val Thr Thr Trp Gln Gly Thr Cys Tyr
                85                  90                  95

Leu Thr Pro Leu Ile Gly Ala Val Leu Ala Asp Ala Tyr Trp Gly Arg
            100                 105                 110

Tyr Trp Thr Ile Ala Cys Phe Ser Gly Ile Tyr Phe Ile Gly Met Ser
        115                 120                 125

Ala Leu Thr Leu Ser Ala Ser Val Pro Ala Leu Lys Pro Ala Glu Cys
130                 135                 140

Ile Gly Asp Phe Cys Pro Ser Ala Thr Pro Ala Gln Tyr Ala Met Phe
145                 150                 155                 160

Phe Gly Gly Leu Tyr Leu Ile Ala Leu Gly Thr Gly Gly Ile Lys Pro
                165                 170                 175

Cys Val Ser Ser Phe Gly Ala Asp Gln Phe Asp Asp Thr Asp Ser Arg
            180                 185                 190

Glu Arg Val Arg Lys Ala Ser Phe Phe Asn Trp Phe Tyr Phe Ser Ile
        195                 200                 205

Asn Ile Gly Ala Leu Val Ser Ser Leu Leu Val Trp Ile Gln Glu
210                 215                 220

Asn Arg Gly Trp Gly Leu Gly Phe Gly Ile Pro Thr Val Phe Met Gly
225                 230                 235                 240

Leu Ala Ile Ala Ser Phe Phe Phe Gly Thr Pro Leu Tyr Arg Phe Gln
                245                 250                 255

Lys Pro Gly Gly Ser Pro Ile Thr Arg Ile Ser Gln Val Val Ala
            260                 265                 270

Ser Phe Arg Lys Ser Ser Val Lys Val Pro Glu Asp Ala Thr Leu Leu
        275                 280                 285

Tyr Glu Thr Gln Asp Lys Asn Ser Ala Ile Ala Gly Ser Arg Lys Ile
290                 295                 300

Glu His Thr Asp Asp Cys Gln Tyr Leu Asp Lys Ala Ala Val Ile Ser
305                 310                 315                 320

Glu Glu Glu Ser Lys Ser Gly Asp Tyr Ser Asn Ser Trp Arg Leu Cys
                325                 330                 335

Thr Val Thr Gln Val Glu Glu Leu Lys Ile Leu Ile Arg Met Phe Pro
            340                 345                 350

Ile Trp Ala Ser Gly Ile Ile Phe Ser Ala Val Tyr Ala Gln Met Ser
        355                 360                 365

Thr Met Phe Val Gln Gln Gly Arg Ala Met Asn Cys Lys Ile Gly Ser
        370                 375                 380

Phe Gln Leu Pro Pro Ala Ala Leu Gly Thr Phe Asp Thr Ala Ser Val
385                 390                 395                 400

Ile Ile Trp Val Pro Leu Tyr Asp Arg Phe Ile Val Pro Leu Ala Arg
                405                 410                 415

Lys Phe Thr Gly Val Asp Lys Gly Phe Thr Glu Ile Gln Arg Met Gly
            420                 425                 430

Ile Gly Leu Phe Val Ser Val Leu Cys Met Ala Ala Ala Ile Val
        435                 440                 445

Glu Ile Ile Arg Leu His Met Ala Asn Asp Leu Gly Leu Val Glu Ser
450                 455                 460

Gly Ala Pro Val Pro Ile Ser Val Leu Trp Gln Ile Pro Gln Tyr Phe
465                 470                 475                 480

Ile Leu Gly Ala Ala Glu Val Phe Tyr Phe Ile Gly Gln Leu Glu Phe
                485                 490                 495
```

```
        Phe  Tyr  Asp  Gln  Ser  Pro  Asp  Ala  Met  Arg  Ser  Leu  Cys  Ser  Ala  Leu
                       500                      505                     510

Ala  Leu  Leu  Thr  Asn  Ala  Leu  Gly  Asn  Tyr  Leu  Ser  Ser  Leu  Ile  Leu
                       515                      520                     525

Thr  Leu  Val  Thr  Tyr  Phe  Thr  Thr  Arg  Asn  Gly  Gln  Glu  Gly  Trp  Ile
                       530                      535                     540

Ser  Asp  Asn  Leu  Asn  Ser  Gly  His  Leu  Asp  Tyr  Phe  Phe  Trp  Leu  Leu
        545                      550                      555                          560

Ala  Gly  Leu  Ser  Leu  Val  Asn  Met  Ala  Val  Tyr  Phe  Phe  Ser  Ala  Ala
                       565                      570                     575

Arg  Tyr  Lys  Gln  Lys  Lys  Ala  Ser  Ser
                       580                      585
```

( 2 ) INFORMATION FOR SEQ ID NO:5:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( i i i ) HYPOTHETICAL: NO ( x i ) SEQUENCE DESCRIPTION: SEQ ID NO:5:

```
        Lys  Lys  Lys  Lys
        1
```

( 2 ) INFORMATION FOR SEQ ID NO:6:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( i i i ) HYPOTHETICAL: NO ( x i ) SEQUENCE DESCRIPTION: SEQ ID NO:6:

```
        Gly  Leu  Gly  Leu
        1
```

( 2 ) INFORMATION FOR SEQ ID NO:7:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( i i i ) HYPOTHETICAL: NO ( x i ) SEQUENCE DESCRIPTION: SEQ ID NO:7:

```
        Thr  Pro  Arg  Lys
        1
```

( 2 ) INFORMATION FOR SEQ ID NO:8:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( i i i ) HYPOTHETICAL: NO ( x i ) SEQUENCE DESCRIPTION: SEQ ID NO:8:

Tyr Gly Gly Phe Leu
1               5

( 2 ) INFORMATION FOR SEQ ID NO:9:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( i i i ) HYPOTHETICAL: NO ( x i ) SEQUENCE DESCRIPTION: SEQ ID NO:9:

Trp His Trp Leu Gln Leu
1               5

( 2 ) INFORMATION FOR SEQ ID NO:10:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( v i ) ORIGINAL SOURCE:
  ( A ) ORGANISM: Arabidopsis thalliana ( x i ) SEQUENCE DESCRIPTION: SEQ ID NO:10:

GCTTCCATGA TTTACGCTGC                                                    20

( 2 ) INFORMATION FOR SEQ ID NO:11:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Arabidopsis thalliana ( x i ) SEQUENCE DESCRIPTION: SEQ ID NO:11:

GCATAAACGC CTACCGG                                                       17